(12) United States Patent
Geske et al.

(10) Patent No.: US 7,092,765 B2
(45) Date of Patent: Aug. 15, 2006

(54) NON-SHEATH BASED MEDICAL DEVICE DELIVERY SYSTEM

(75) Inventors: Jeff B. Geske, Fridley, MN (US); Steven L. Waldhauser, Circle Pines, MN (US); Bruce E. Chivers, Minneapolis, MN (US); James F. Kelley, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 676 days.

(21) Appl. No.: 10/252,243

(22) Filed: Sep. 23, 2002

(65) Prior Publication Data
US 2004/0059348 A1    Mar. 25, 2004

(51) Int. Cl.
*A61N 1/372* (2006.01)

(52) U.S. Cl. ..................... 607/122; 607/116

(58) Field of Classification Search .............. 606/129; 607/116, 122
See application file for complete search history.

(56) References Cited

U.S. PATENT DOCUMENTS

| | | | |
|---|---|---|---|
| 3,735,650 A | 5/1973 | Weng, Jr. | |
| 4,355,646 A | 10/1982 | Kallok et al. | |
| 4,627,420 A | 12/1986 | Katz | |
| 4,799,499 A | 1/1989 | Bisping | |
| 4,944,088 A | 7/1990 | Doan et al. | |
| 5,003,990 A * | 4/1991 | Osypka | 600/585 |
| 5,036,854 A * | 8/1991 | Schollmeyer et al. | 600/374 |
| 5,320,627 A | 6/1994 | Sorensen et al. | |
| 5,443,492 A | 8/1995 | Stokes et al. | |
| 5,601,600 A * | 2/1997 | Ton | 606/206 |
| 5,683,399 A | 11/1997 | Jones | |
| 5,713,867 A | 2/1998 | Morris | |
| 5,713,868 A | 2/1998 | Fussman | |
| 5,772,669 A * | 6/1998 | Vrba | 623/1.11 |
| 5,873,842 A | 2/1999 | Brennen et al. | |
| 5,876,431 A | 3/1999 | Spehr et al. | |
| 5,902,331 A | 5/1999 | Bonner et al. | |
| 5,964,793 A | 10/1999 | Rutten et al. | |
| 5,984,944 A * | 11/1999 | Forber | 606/191 |
| 6,010,526 A * | 1/2000 | Sandstrom et al. | 607/1 |
| 6,072,154 A | 6/2000 | Maynard | |
| 6,129,749 A | 10/2000 | Bartig et al. | |
| 6,185,464 B1 | 2/2001 | Bonner et al. | |
| 6,224,586 B1 | 5/2001 | Stephens | |
| 6,277,107 B1 | 8/2001 | Lurie et al. | |

(Continued)

FOREIGN PATENT DOCUMENTS

EP    0000280 A1    1/1979

(Continued)

*Primary Examiner*—George Manuel
*Assistant Examiner*—Nicole R. Kramer
(74) *Attorney, Agent, or Firm*—Girma Walde-Michael; Daniel G. Chapik; Michael C. Soldner

(57) ABSTRACT

A non-sheath based medical device delivery system is provided including an elongated tubular guide body having a distal end fixedly attached to a resilient collet with a longitudinal opening to receive a medical lead or other device. The collet may be opened by actuating a retraction member to cause the closing member to slide proximally along the collet shaft, allowing the collet to maintain a normally open position. With the collet closed, the device may be advanced to a desired internal body location by advancing the guide body. The majority of the device body will be exposed, running alongside the guide body, allowing any sensors or electrodes located on the device body to be fully operational during the implantation procedure. The delivery system may be removed by opening the collet, to slidably disengage from the device body.

49 Claims, 16 Drawing Sheets

U.S. PATENT DOCUMENTS

| | | | |
|---|---|---|---|
| 6,277,125 B1 * | 8/2001 | Barry et al. | 606/108 |
| 2002/0077686 A1 | 6/2002 | Westlund et al. | |
| 2004/0077999 A1 * | 4/2004 | Selmon et al. | 604/104 |

FOREIGN PATENT DOCUMENTS

| | | |
|---|---|---|
| EP | 0656193 B1 | 6/1995 |

* cited by examiner

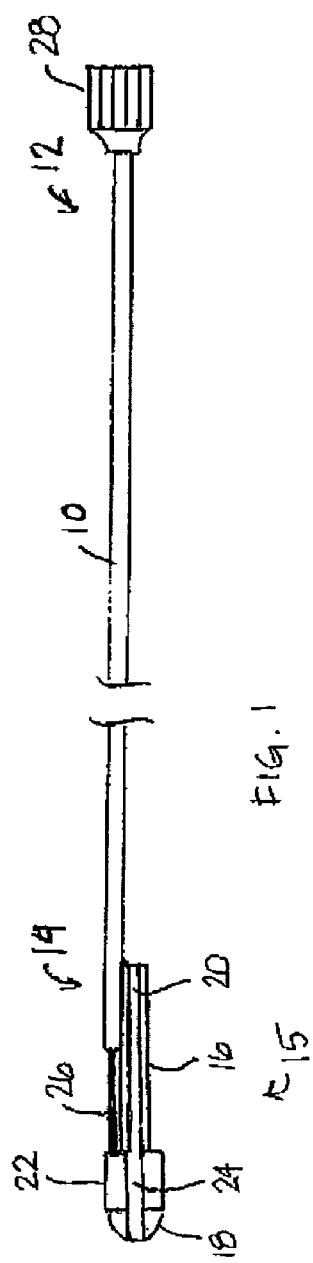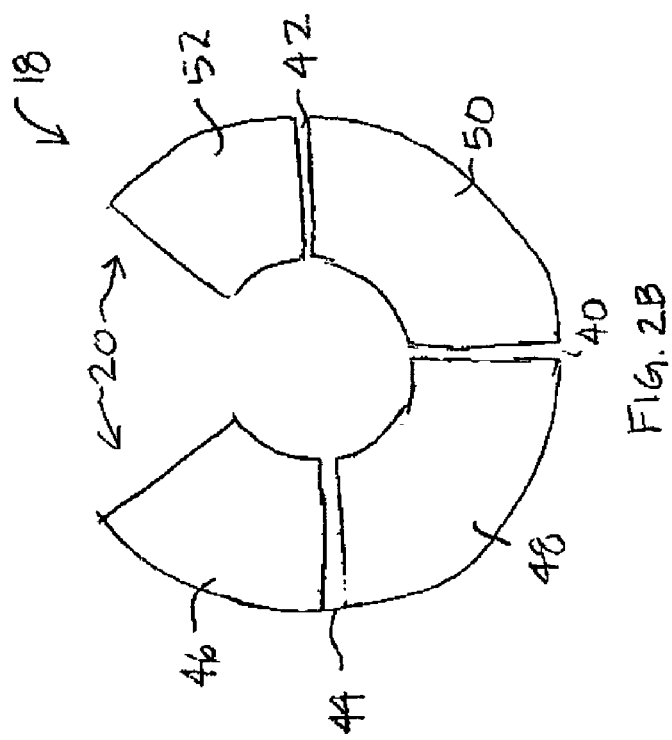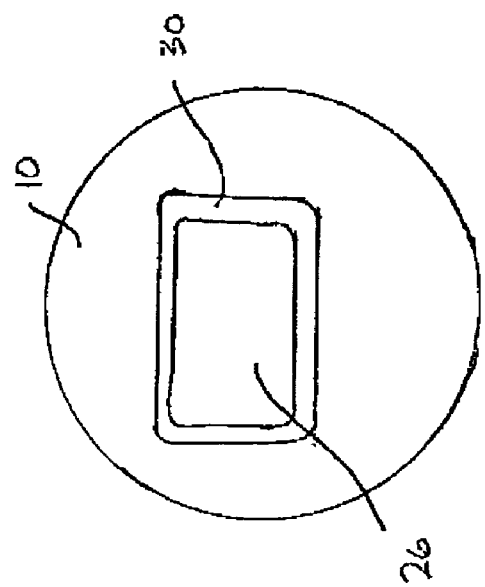

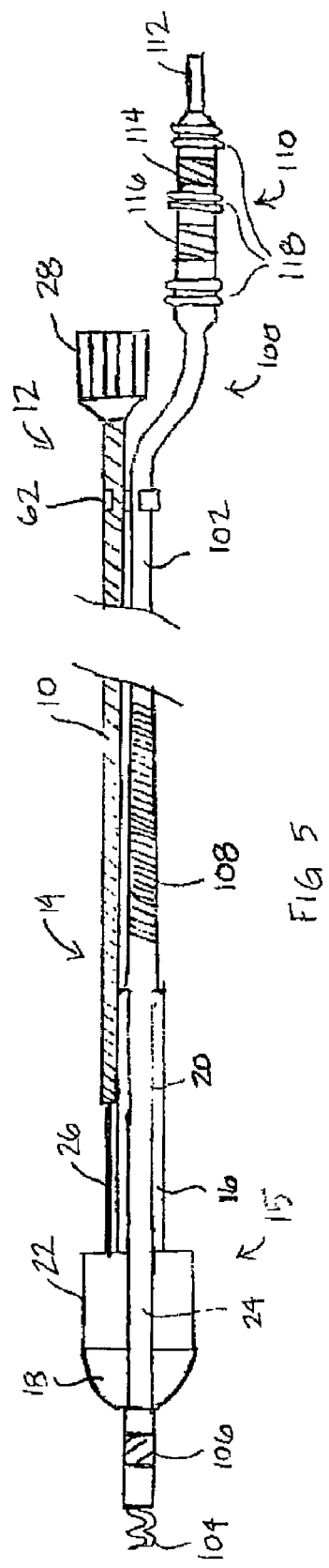
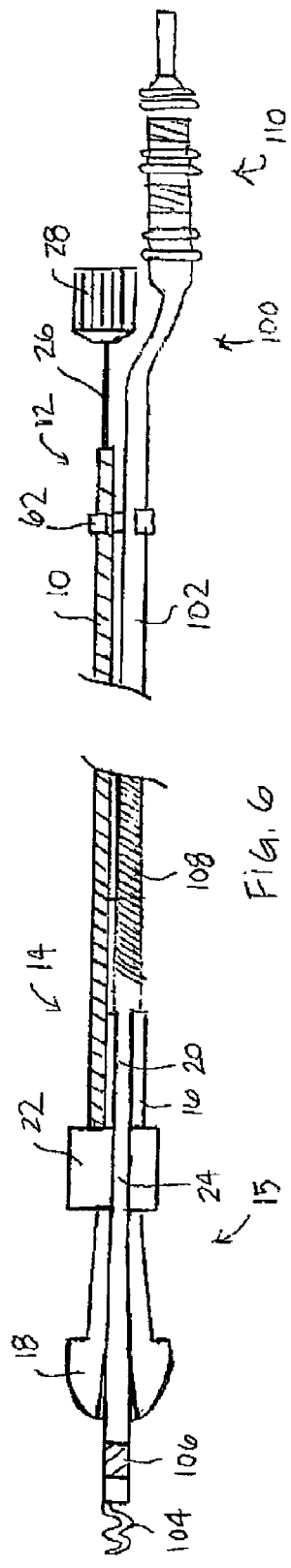
Fig. 5
Fig. 6

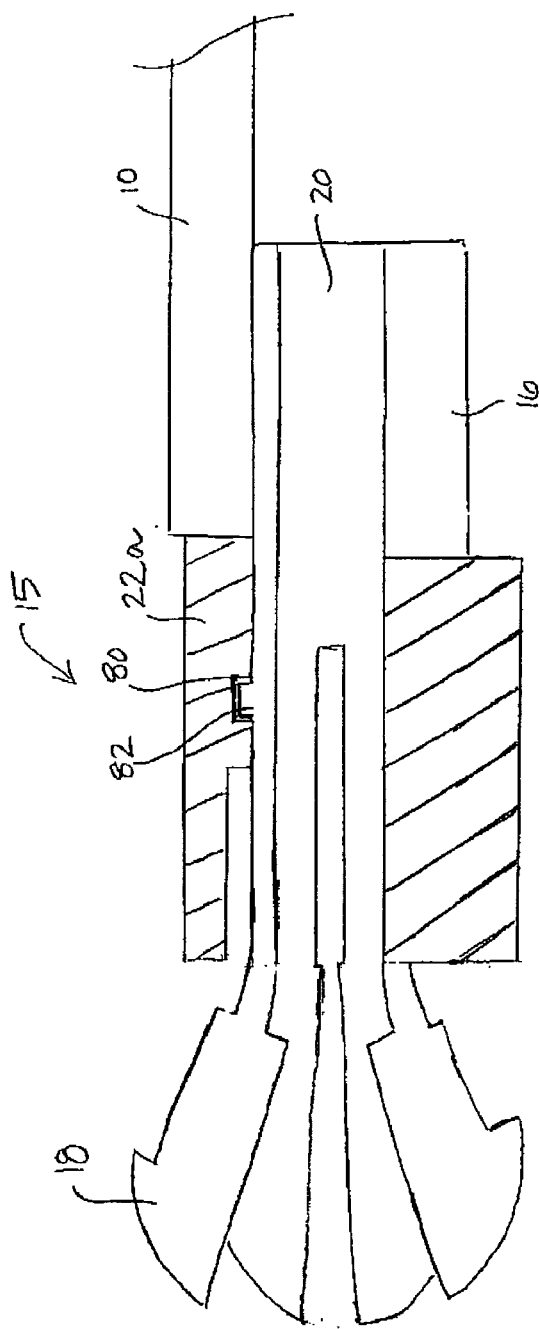
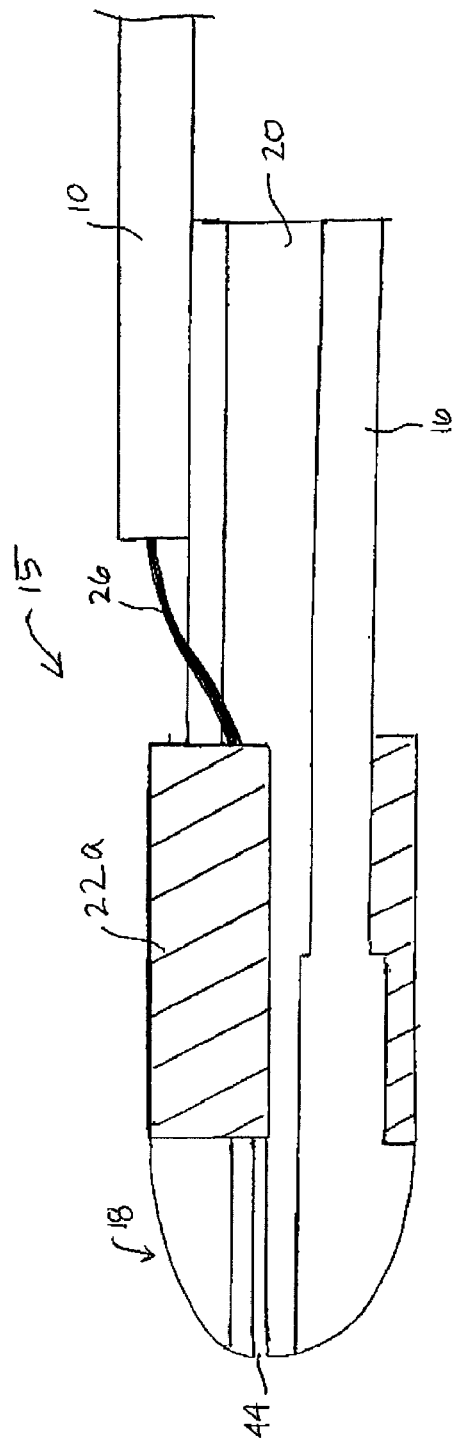

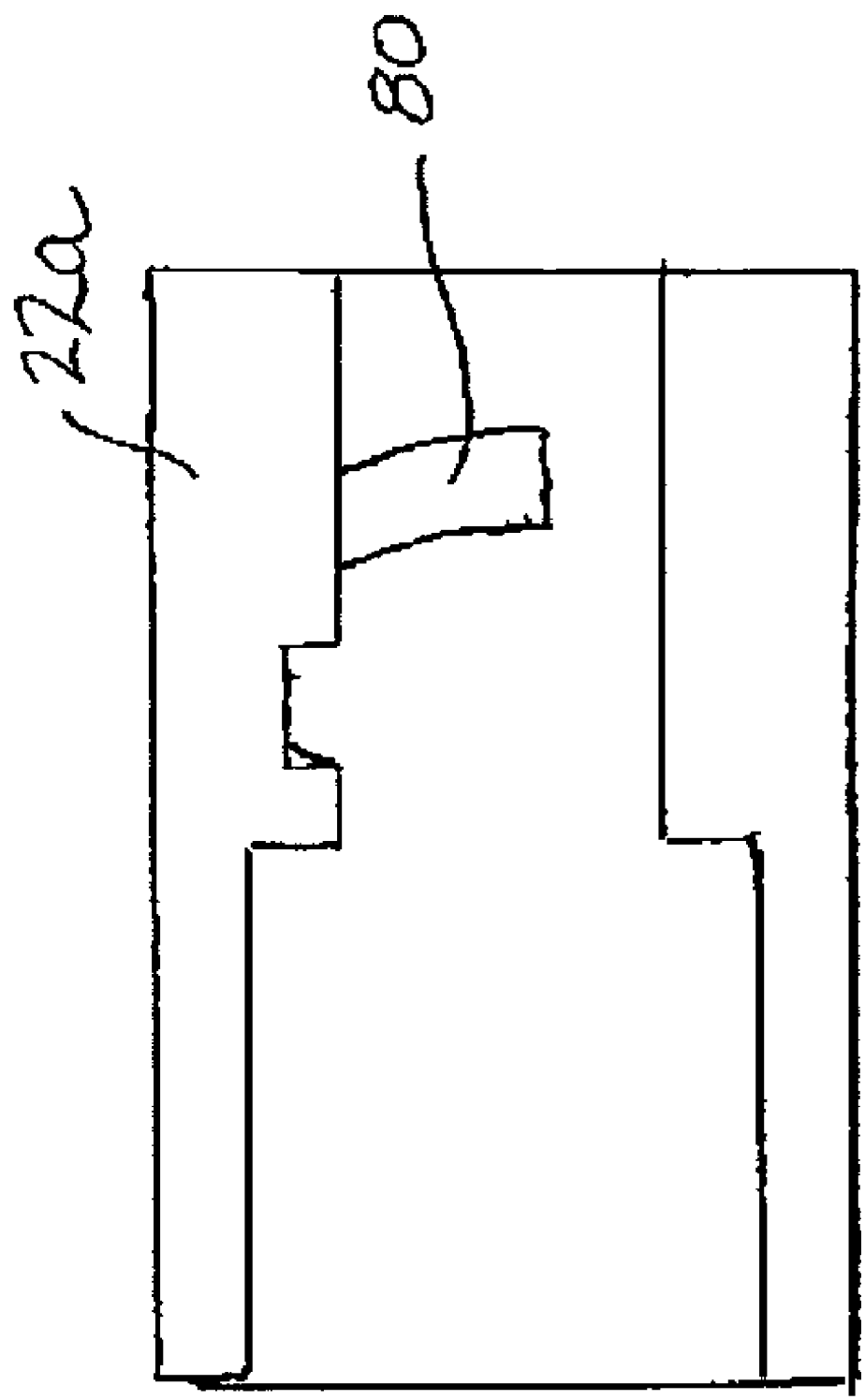

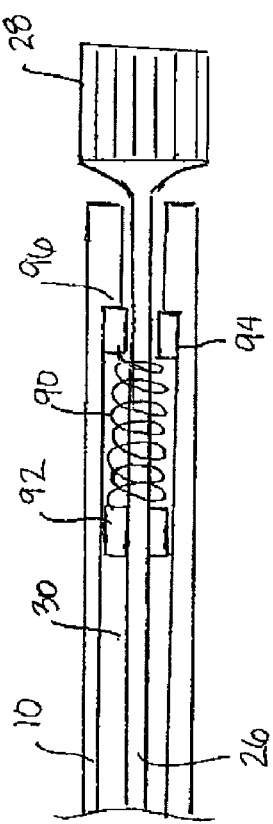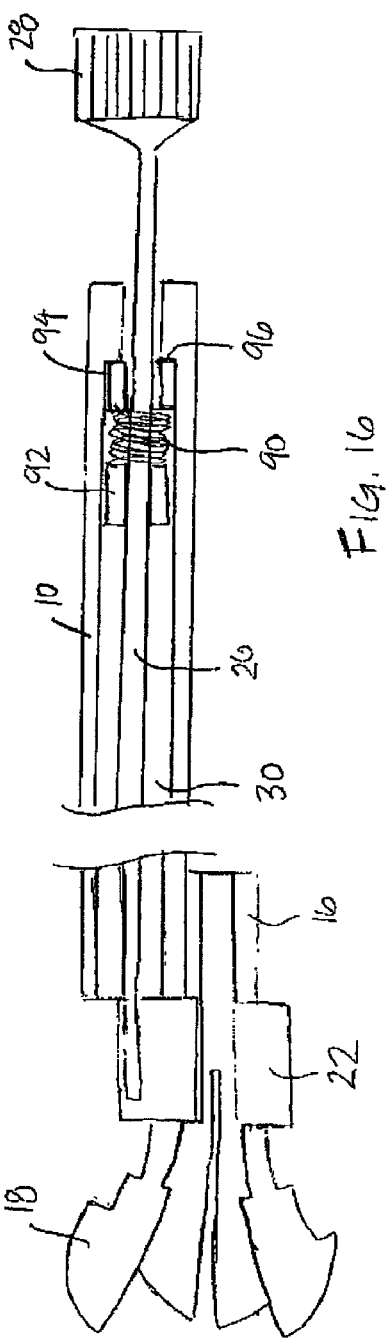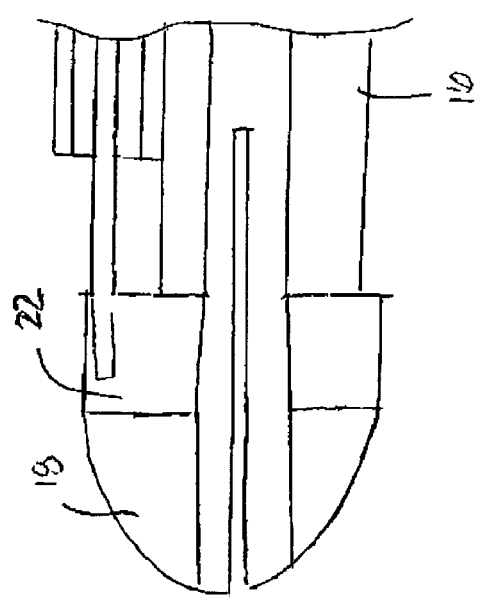

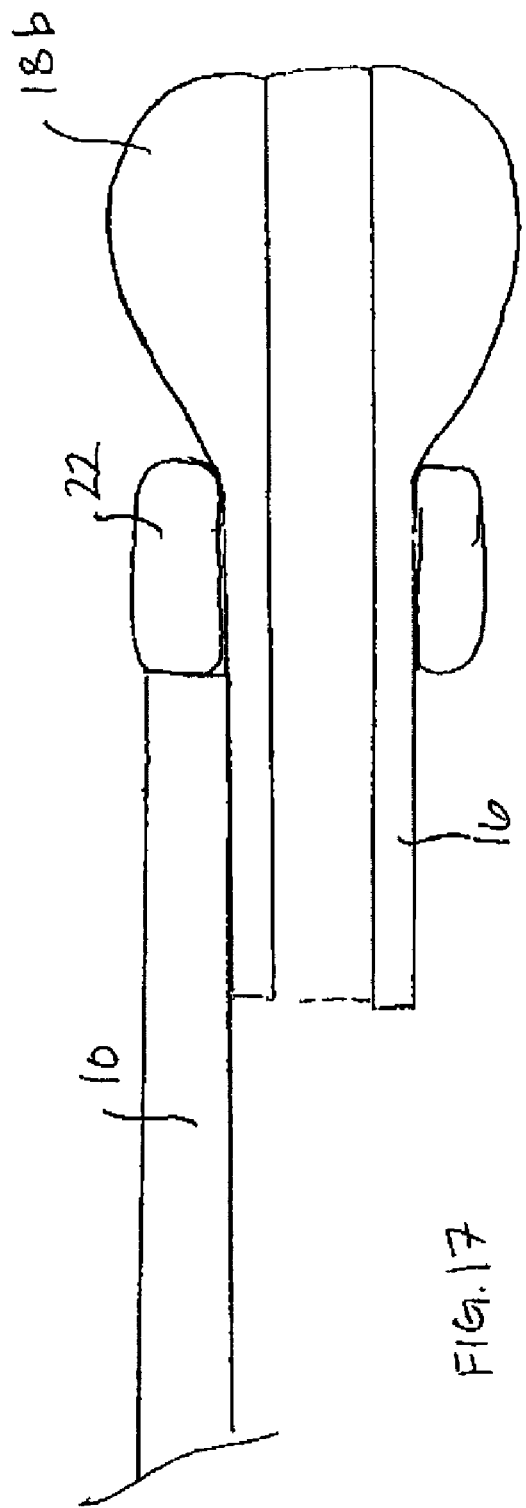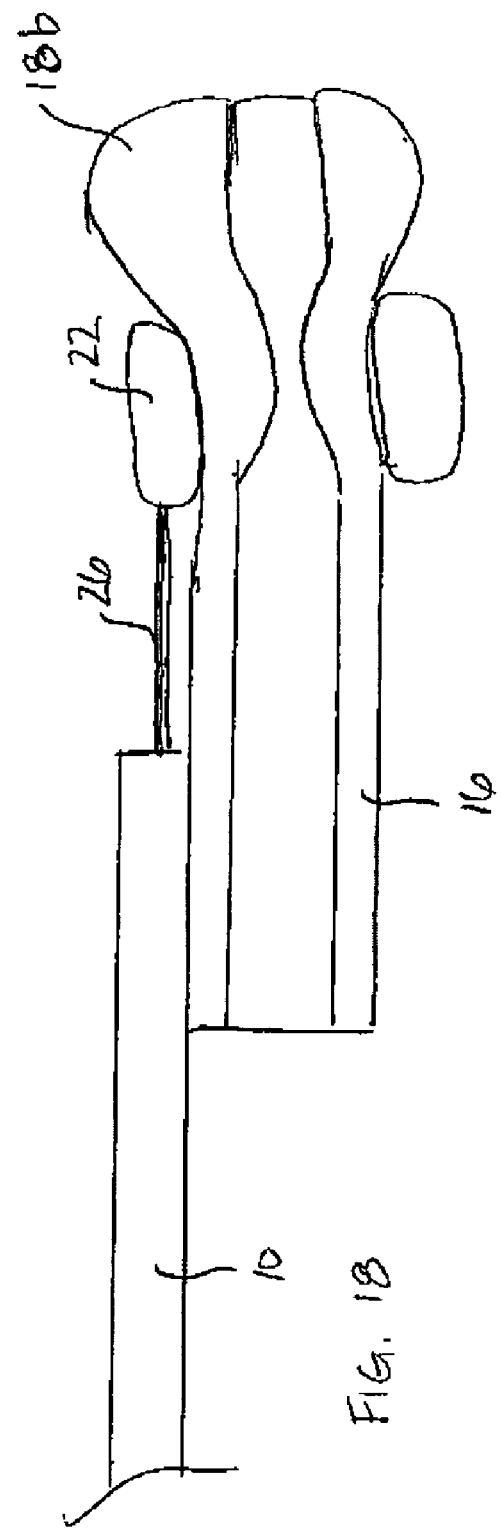

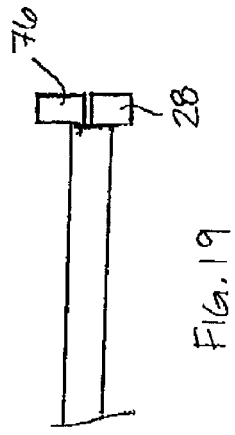
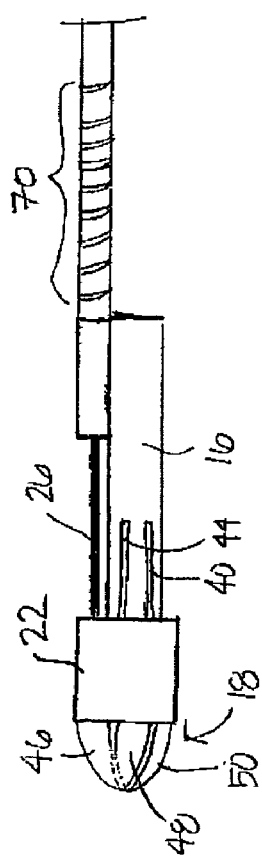
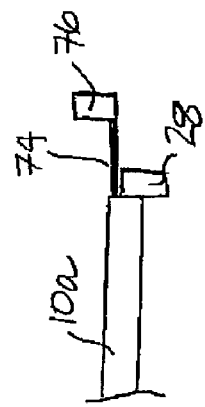
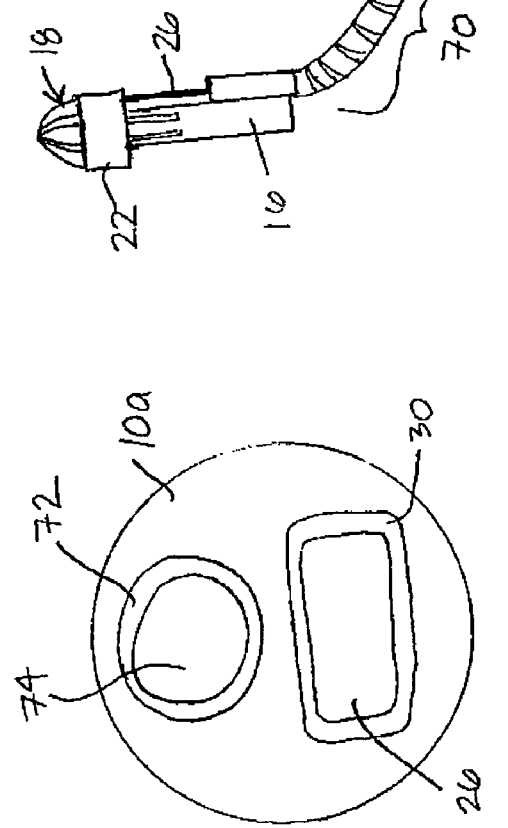

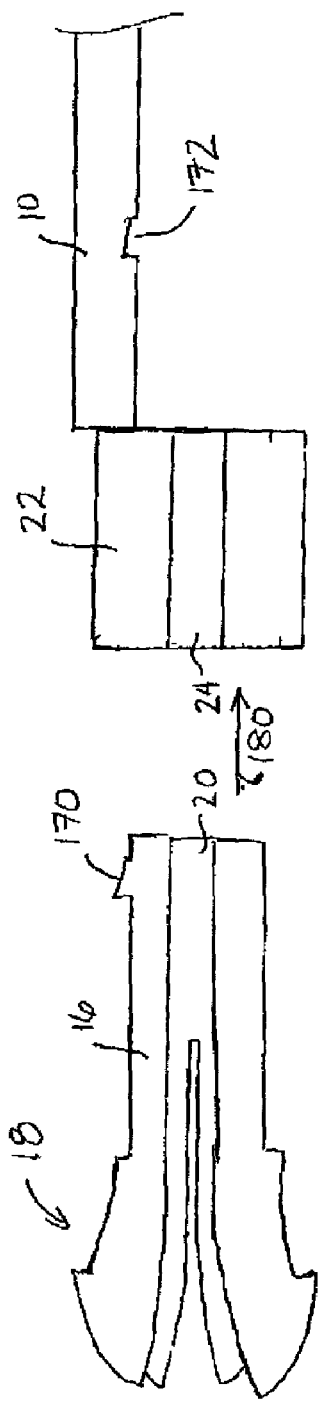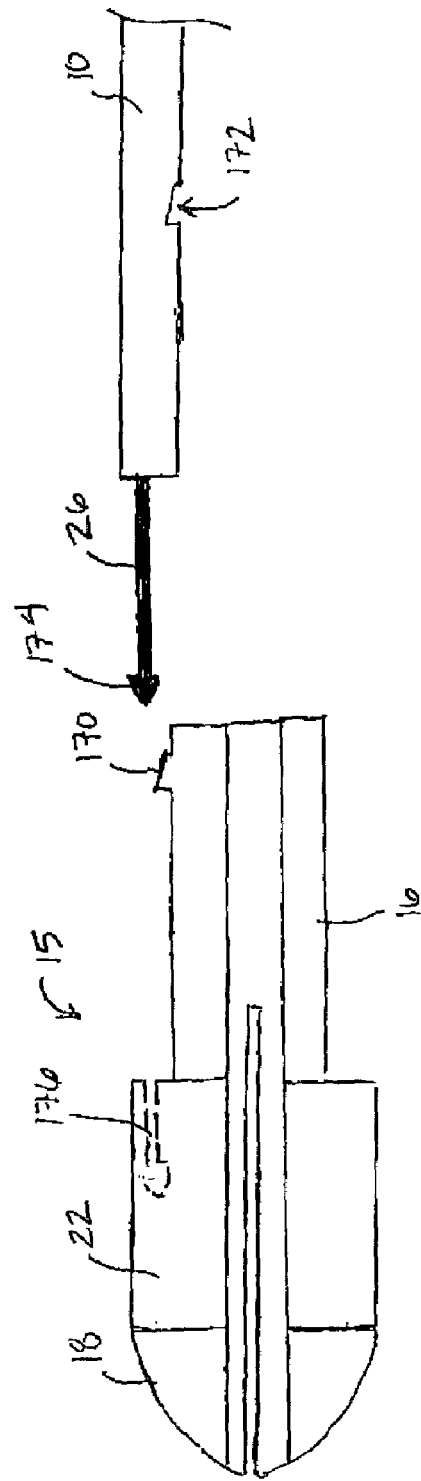

NON-SHEATH BASED MEDICAL DEVICE DELIVERY SYSTEM

FIELD OF THE INVENTION

The present invention relates to medical device delivery systems for introducing medical devices into an internal body space. More specifically, the present invention relates to a non-sheath based medical device delivery system particularly suited for introducing cardiac leads, or other specialized medical devices into the heart, coronary sinus or cardiac veins.

BACKGROUND OF THE INVENTION

Various specialized medical devices, such as cardiac leads, ultrasonic catheters, balloon angioplasty catheters, ablation catheters, electrophysiological diagnostic catheters, pressure monitoring catheters etc., require the use of a delivery system for deploying the device in a desired internal body space, such as the heart or vascular system. Delivery systems can include an introducer and guide catheter, which are typically tubular, sheath-based systems. A guide catheter may be advanced to a desired internal body location, and a medical device deployed through a central lumen of the catheter.

Cardiac leads are often placed in contact with the cardiac tissue by passage through a venous access, such as the subclavian vein, the cephalic vein, or one of its tributaries, using an introducer and guide catheter. In such a manner, transvenous leads may advantageously be placed in contact with the heart without requiring major thoracic surgery. A multi-step procedure is generally required to introduce such leads within the venous system. Generally this procedure consists of inserting a hollow needle into a blood vessel, such as the subclavian vein. A wire guide is then passed through the needle into the interior portion of the vessel. The needle is then withdrawn and an introducer sheath is inserted over the wire guide into the vessel. The introducer is advanced into a suitable position within the vessel, i.e. so that the distal end is well within the vessel but the proximal end is outside the patient. Next the wire guide is removed. The introducer is left in position and therefore offers direct access through its hollow lumen from outside the patient to the interior of the blood vessel. For a description of these general procedures, reference is made to U.S. Pat. No. 5,713,867 issued to Morris, incorporated herein by reference in its entirety.

A guide catheter may be advanced through the venous access provided by the introducer to reach a monitoring or treatment site within the cardiovascular system. A cardiac lead, or other specialized medical device, may then be passed through the guide catheter to reach the desired location. Cardiac leads, which are highly flexible, are sometimes advanced over a guidewire or stylet that provides the lead with the stiffness needed to advance it through a venous pathway. This multi-step procedure can thus require several tools and requires considerable skill to perform.

After the lead is satisfactorily positioned, the guide catheter can be removed. One limitation of a sheath-based delivery system is that a sheath enclosing a lead generally cannot be removed over a standard cardiac lead connector assembly. Cardiac leads typically have a relatively bulky connector assembly that can be 1 to 3 times wider than the lead body at the proximal end. Therefore, cardiac leads are commonly introduced using a splittable or slittable introducer or guide catheter so that the sheath may be removed from around the lead by being slit apart. In such a manner the sheath does not have to be removed over the relatively bulky connector assembly at the proximal end of the lead. A slittable introducer sheath is disclosed in the above referenced U.S. Pat. No. 5,713,868. A slittable guiding introducer is described in U.S. Pat. No. 6,277,107 issued to Lurie et al. Slitting a guide catheter generally requires a slitting tool and can be a time-consuming task.

After being split apart and removed, a guide catheter cannot be reused and is discarded. Thus such split or slit guide catheters are normally single-use devices. A further limitation of using a slittable guide catheter, therefore, is that, if additional leads or devices need to be placed during the same surgical procedure, a new guide catheter is required. Furthermore, a situation sometimes arises that requires repositioning of an implanted cardiac lead. A lead may need to be repositioned, for example, when unacceptable thresholds for pacing or defibrillation are measured during an implant procedure or later after the lead has been chronically implanted.

Repositioning an implanted lead normally requires that the lead be removed from the patient's body and guided to a new implant site using the same multi-step process described above utilizing a new guide catheter. The proximal connector assembly on the implanted lead prevents an introducer or guide catheter from being inserted over the implanted lead to allow repositioning while the lead is still within the patient's body.

A further limitation of a sheath-based guide catheter is that the guide catheter can add a substantial increase to the overall diameter of the device as it is being delivered. Recent interest in pacing in the left heart chambers has led to the development of small diameter coronary sinus and cardiac vein leads. These leads are typically placed by advancing a guide catheter into the coronary sinus ostium, then advancing the lead into the coronary sinus and further into a cardiac vein as desired. Guide catheters may be too large in diameter to be advanced further than the coronary sinus or cardiac veins. Because a cardiac lead must be highly flexible in order to withstand the beating motion of the heart, a stylet or guidewire passed through a central lumen of the lead is often required in order to provide the lead with the stiffness needed to advance the lead further into the cardiac veins, without the support of the guide catheter. However, requiring a central lumen for a guidewire or stylet increases the size requirement of the lead. A guidewire or stylet may not provide effective torque transfer needed for fixing a lead by rotation.

Yet another limitation of sheath-based delivery systems is that the cardiac lead or other medical device being introduced may include sensors or electrodes along the body of the lead or device, which are enclosed within the guide catheter sheath. During the implant procedure, as long as the guide catheter is in place, these electrodes or sensors are not available for making measurements that may be of interest. For example, a cardiac defibrillation lead generally includes one or more defibrillation coils carried on the lead body. In order to verify that a lead position is acceptable, defibrillation thresholds are generally measured by inducing an arrhythmia after placing the lead and delivering defibrillation therapy through the defibrillation coil(s). A guide catheter sheath would need to be removed from the lead in order to perform these tests. If the defibrillation thresholds are unacceptable, the lead will need to be repositioned. If the guide catheter has already been removed, the lead must be removed and repositioned after placement of a new guide catheter.

Other types of sensors may be provided along the body of a lead or medical device, such as electrogram sensing electrodes, ultrasonic sensors, pressure sensors, etc. These sensors could be used for making measurements during an implant procedure to provide diagnostic or other information to and aid the physician in identifying and/or selecting an optimal implant site for the medical device.

To address some of these limitations, various non-sheath based delivery systems have been described. For example, U.S. Pat. No. 6,185,464 to Bonner et al. describes an arrangement for introducing and implanting an endocardial lead that includes pusher means for advancing a cardiac lead transvenously alongside a guide body. In this arrangement, a guide body tracking and cardiac lead engaging means includes a guide body tracking lumen that engages the guide body and a lead body receiving lumen that tightly grasps a lead body in a normal clamped state. By expanding the guide body tracking lumen, effected by an expandable balloon, the lead body receiving lumen is expanded to receive or release a lead body.

U.S. Pat. No. 6,129,749 issued to Bartig et al. discloses a pacing lead having a molded support body at its distal end, which supports an electrode and includes a lumen for a guidewire. This additional feature increases the size of the distal end of the lead. Additional features on the medical device itself are generally undesirable because these features may increase the cost or complexity of manufacturing the device. An additional feature for engaging a delivery device may not be a standard feature of many medical devices, limiting the utility of a delivery system requiring such a feature to only certain devices equipped with that additional feature.

Medical therapy or diagnostic devices may also need to be delivered to an internal body organ or space through an open surgical approach rather than a vascular approach. For example, in order to place an epicardial lead on the heart, a thoracotomy is generally required to approach the heart. Still some areas of the heart may be difficult to approach, even through a thoracotomy, requiring a larger incision or lifting or moving of the heart itself. A medical device delivery system that allows a device to be guided to an internal body location, such as the epicardial surface, through minimally sized incision can reduce the invasiveness and difficulty of the procedure.

Furthermore, a medical device may need to be inserted at a depth within the targeted tissue, requiring a small incision or stab wound into the tissue to place the medical device. A hollow, splittable needle is described in U.S. Pat. No. 5,443,492, issued to Stokes, for application of an active fixation lead into the epicardial heart tissue. The lead is carried in the lumen of the hollow needle to aid in inserting the distal end of the lead into the heart tissue but the needle is not used for guiding the lead to the implant site. In order to make the small incision or stab wound that may be required to place a medical device, a larger skin incision may sometimes be required to enlarge the open approach to the site to perform these procedures. A delivery system that allows a stab wound to be made without a fully open approach may reduce the invasiveness of such a procedure and allow a device to be more easily guided to and inserted into a desired tissue site.

It is desirable, therefore, to provide an improved non-sheath based medical device delivery system that allows electrodes, sensors, or other components mounted on a lead or catheter body to be exposed and operational during a surgical procedure. It is further desirable that such a system may be provided at a reduced size to allow delivery of small diameter cardiac leads or other devices into small diameter vessels. It is also desirable that a medical device delivery system be capable of guiding and, if necessary, inserting a medical device into a tissue site. A medical device delivery system should be easily mounted on or removed from the body of a medical device, without requiring complicated system components or special features on the medical device body. Moreover, it is desirable that the delivery system be removable from a medical device without slitting, splitting or otherwise rendering the device unusable for delivering multiple devices during a single surgical procedure or repositioning a device without first having to remove the device from the patient's body.

SUMMARY OF THE INVENTION

The present invention addresses the above described needs by providing a non-sheath based medical device delivery system. The delivery system includes a closable collet designed to engage a medical lead or other device near its distal end. The collet is mounted on an elongated, tubular guide body. A closing member, provided as a ring encircling at least a portion of the collet circumference, closes the collet when advanced to a distal position on the collet. Retracting the closing member to a proximal position on a collet shaft allows the collet to open. The closing member position is controlled by actuating a retraction member that is attached at its distal end to the closing member and extends through the guide body, exiting the guide body proximal end.

The collet and closing member are preferably provided with aligned longitudinal openings for receiving or removing a lead or device. When a lead or other device is mounted in the collet and closing member assembly, the elongated body of the device lies adjacent the guide body and is exposed along its entire length with only a portion of its circumference enclosed within the collet and closing member assembly.

In one embodiment, the collet is provided with an atraumatic shape, such as a projectile or bullet-nose shape, at its distal end such that the distal tip does not cause damage to anatomical structures as it is advanced. In an alternative embodiment, the collet is provided with a pointed or needle-like tip to allow the delivery system to be used as a "stab-in" device for placing a lead or other medical device at a depth within a tissue, such as an epicardial lead.

A method for using the delivery system includes inserting a medical device into the collet and closing member assembly and closing the collet by advancing the closing member such that the collet is fixedly engaged with the device body. The device may be guided to an implant location by advancing the guide body of the delivery system along a desired pathway. The distal end of the guide body may be preformed or shapeable to aid in steering or navigating the device to a desired implant site. Alternatively, the guide body may be constructed from a shape memory alloy or polymer, or the guide body may be provided with a flexible distal end that may be deflected with the use of a pull wire to allow steering of the guide body around obstacles. During advancement of the device, electrophysiological measurements or other sensor measurements may be performed using sensors on the device body, if present, to provide diagnostic data or to aid in selecting an implant site.

Once the device is properly positioned, the collet is opened by actuating the retraction member to cause retraction of the closing member. With the collet open, the collet and closing member assembly may easily slide over the device body. The delivery system may then be removed by sliding the collet and closing member assembly over the device body in a proximal direction and removing the device body through the aligned longitudinal openings of the collet and closing member.

If device repositioning is required, the collet and closing member assembly may be inserted back over the device body and, with the collet in an open position, slid to the distal end of the device by advancing the guide body adjacent the device body. Once near the distal end of the device, the collet may be closed onto the device body allowing the device to be removed from the current implant site and moved to a new implant site using the delivery system.

A delivery system provided by the present invention may further be used for tunneling a device under the skin. The proximal connector assembly of a chronically implantable lead generally needs to be tunneled to a subcutaneous pocket wherein an implantable pulse generator, such as a pacemaker or implantable cardioverter defibrillator, will be implanted. The delivery system may be inserted over the proximal connector assembly of a lead to tunnel it subcutaneously to an associated device to which it will be connected.

The delivery system provided by the present invention thus allows a medical device to be guided to an implant site while maintaining exposure of sensors or electrodes mounted on the device body for making measurements during the implant procedure. The delivery system may be easily removed from a device body and still be reused if repositioning of the device is necessary. The system may be constructed to accommodate varying sizes of medical devices without requiring special features on the medical device itself. The diameter of the collet and closing member assembly of the delivery system may be minimized to fit a small diameter device, reducing the overall diameter of the system such that it may be used to advance small diameter leads or other devices through narrow vessels or body spaces.

BRIEF DESCRIPTION OF THE DRAWINGS

FIG. 1 is a plan view of a non-sheath based medical device delivery system according to the present invention.

FIG. 2A is a cross-sectional view of a guide body included in the medical device delivery system of FIG. 1.

FIG. 2B is an end view of the collet included in the medical device delivery system of FIG. 1.

FIG. 5 is a plan view of the delivery system of FIG. 1 in which the collet and closing member assembly is closed around a cardiac lead body.

FIG. 6 is a plan view of the delivery system and cardiac lead of FIG. 5 in which the collet is in an open position around the cardiac lead body.

FIG. 12 is a plan view of an alternative embodiment of a collet and closing member assembly wherein the closing member is rotatable with respect to the collet and collet shaft.

FIG. 13 is a side view of the closing member of FIG. 12.

FIG. 14 is a plan view of the collet and closing member assembly of FIG. 12 wherein the closing member has been advanced axially to close the collet and to at least partially close the collet longitudinal opening.

FIG. 15 is a partially cut-away, side view of an alternative embodiment of a delivery system wherein the retraction member is provided as a spring-loaded member.

FIG. 16 is a partially cut-away, side view of the delivery system of FIG. 15 showing the spring member in a compressed state.

FIG. 17 is a side, partially cut-away view of an alternative embodiment of a collet and closing member assembly that may be included in the delivery system of FIG. 1.

FIG. 18 is a side, partially cut-away view of the collet and closing member assembly of FIG. 17 in a closed position.

FIG. 19 is a plan view of an alternative embodiment of the delivery system of the present invention in which the guide body is further equipped with a pull wire to aid in steering the delivery system along a tortuous pathway.

FIG. 20 is a cross-sectional view of the guide body included in the delivery system shown in FIG. 19.

FIG. 21 is a plan view of the delivery system of FIG. 19 showing deflection of the distal end of the guide body using a pull wire.

FIG. 23 is plan view of the distal end of a delivery system according to an alternative embodiment of the present invention in which the components are provided as disassembled, interlocking components.

FIG. 24 is a plan view of the distal end of an alternative embodiment of a delivery system having interlocking components.

DETAILED DESCRIPTION OF THE INVENTION

Figure 3:
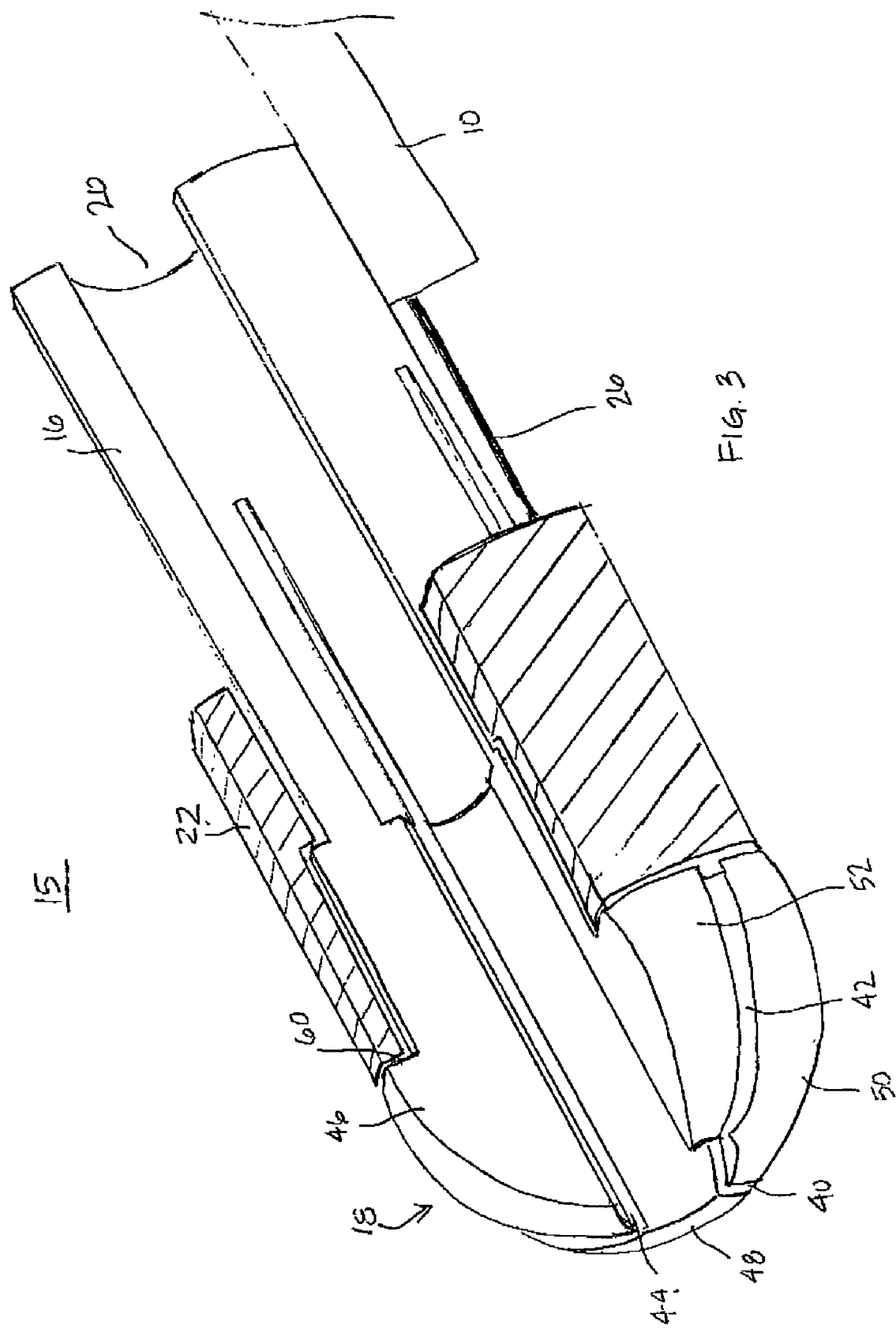
FIG. 3 is a perspective view of the collet and closing member assembly included in the system of FIG. 1 wherein the collet is shown in a closed position.

As indicated above, the present invention is directed toward providing a non-sheath based medical device delivery system. The system to be described herein is intended for delivering or repositioning specialized medical devices having an elongated body, such as cardiac pacing leads or other therapy delivery or diagnostic devices. Other specialized medical devices with which the system may be used, for example, may include various types of catheters or sensors such as angioplasty catheters, ablation catheters, pressure monitoring catheters, electrophysiological diagnostic catheters, ultrasonic catheters, drug delivery catheters, cell delivery catheters, fluid delivery catheters, oxygen sensors, etc. Such devices may have electrodes or other sensors located along the length of the device body, which will remain exposed and operational during a device delivery procedure using the delivery system provided by the present invention. The delivery system may be used for delivering medical devices into the heart or vascular system. The delivery system may also be well-suited for delivering devices to other internal body spaces such as within the digestive tract, urinary tract, reproductive tract, neuromuscular system, central nervous system, or otherwise.

FIG. 1 is a plan view of a non-sheath based medical device delivery system according to the present invention. The delivery system includes an elongated, tubular guide body 10 having a proximal end 12 and a distal end 14. The distal end 14 is preferably fixedly attached to a hollow shaft 16 of a collet 18 provided for engaging a medical device. A collet and closing member assembly 15 includes shaft 16 and collet 18 and a closing member 22. Closing member 22 is mounted on collet 18 and generally takes the form of a substantially 'C' shaped ring encircling at least a portion of the circumference of collet 18. Closing member 22 is moveable in an axial direction with respect to collet 18, preferably within a physically constrained range.

A retraction member 26 is used to control the movement of closing member 22. Retraction member 26 is fixedly attached at its distal end to closing member 22 and extends through the entire length of guide body 10, exiting the proximal guide body end 12. Actuation of retraction member 26, which may involve pulling, pushing or rotating retraction member 26, causes axial movement of closing member 22, thereby opening or closing collet 18 as will be described in greater detail herein. Retraction member 26 may optionally be provided with an actuating member 28 at its proximal end. Actuating member 28 may be provided as a handle for a physician to grasp when pulling, pushing, rotating or otherwise actuating retraction member 26. Actuation of retraction member 26 may also involve heat or electrical activation of shape memory material included in retraction member 26. Actuating member 28 may be used to provide the thermal or electrical activation energy required.

Guide body 10 may be formed of a biocompatible material such as stainless steel, polyurethane, a fluoropolymer, or other material having the appropriate balance of stiffness and flexibility required to allow guide body 10 to be advanced along a vascular or other internal pathway and be maneuvered past obstacles encountered such as curves or branches. In one embodiment, guide body 10 may be provided as a malleable stainless steel such that the distal end may be bent or curved to aid in guiding a lead or other medical device to a desired site, such as into the coronary sinus or a desired cardiac vein. Guide body 10 may alternatively be formed from a polymeric material having a preformed curve or bend near its distal end 14. Guide body 10 may additionally be provided with a shape memory material such as Nitinol or a shape memory polymer that may be used to shape the distal end of guide body 10 to aid in maneuvering the delivery system.

Guide body 10 is fixedly attached to shaft 16 of collet 18 by welding, bonding or other appropriate methods, depending on the material from which guide body 10 and shaft 16 are formed. Collet 18 and shaft 16 may be formed as a single component formed from a relatively rigid biocompatible material such as stainless steel, Delrin®, a polyurethane, a fluoropolymer, or other material.

FIG. 2A is a cross-sectional view of guide body 10. Guide body 10 may be provided with a generally circular cross-section. Guide body 10 could conceivably be provided with a generally oval or generally polygonal cross-section as well. Retraction member 26 is preferably a flat wire, as shown in FIG. 2A, or may alternatively be a generally round wire. Guide body 10 is provided with a lumen 30 to accommodate retraction member 26. Lumen 30 may be generally square or rectangular in cross-section to accommodate a flat wire retraction member 26 or may be generally circular to accommodate a generally round wire retraction member. By providing retraction member 26 as a flat wire carried in a correspondingly shaped lumen 30, rotation of member 26 within lumen 30 is prevented. Rotation of retraction member 26 within lumen 30 may result in undesired rotation of closing member 22 with respect to collet 18. Such rotation may cause partial closure of a longitudinal opening 20 provided on collet 18 and shaft 16 to receive a lead or device body.

Closing member 22, shown in FIG. 1, is preferably formed from stainless steel and may alternatively be formed from another generally rigid material such as Delrin, or other high durometer polymer. Retraction member 26 is preferably formed from a minimally extensible stainless steel wire. Retraction member 26 may be fixedly attached to closing member 22 by welding, bonding or other appropriate methods depending on the material from which member 26 and closing member 22 are made. Retraction member 26 may alternatively be provided as a cable or high tensile strength, minimally extensible fiber. Retraction member 26 may also be provided as contractable wire formed from a thermally or electrically-activated shape memory material which, when actuated, causes member 26 to contract.

Collet 18 and hollow shaft 16 are preferably provided with longitudinal opening 20 through which a lead or device body may be received or removed. Closing member 22 is provided with a corresponding longitudinal opening 24 in alignment with opening 20. As described above, closing member 22 preferably does not rotate with respect to collet 18 to maintain the alignment of longitudinal opening 24 and closing member opening 20 to allow a lead or other device to be easily inserted or removed from the collet and closing member assembly 15.

Longitudinal opening 20 may be provided as an approximately 90 degree angle channel cut into shaft 16 and collet 18. Longitudinal opening 20 could also be a wider or narrower opening but should preferably be, generally, wide enough to allow insertion of a lead or device body yet narrow enough that the lead or catheter body once inserted, is retained within the collet and closing member assembly 15 and does not easily fall out. The size of longitudinal opening 20 will depend on the size of the device body with which the delivery system is intended to be used. Longitudinal opening 20 aligned with opening 24 allows the entire length of a lead or device body to be exposed with only a portion of the body circumference enclosed by the collet and closing member assembly 15.

FIG. 2B is an end view of a collet included in the medical device delivery system of FIG. 1. In addition to longitudinal opening 20, collet 18 includes at least one, preferably two or more and more preferably three open channels 40, 42 and 44, which separate a corresponding number of parting members 46, 48, 50 and 52. Channels 40, 42 and 44 extend longitudinally through collet 18 and may extend through a portion of shaft 16.

FIG. 3 is a perspective view of the collet and closing member assembly 15 wherein the collet is shown in a closed position. The internal diameter of collet 18 in a closed position is preferably sized to form a friction fit with the outer diameter of a lead or device body with which the delivery system is to be used such that the lead or device is firmly grasped by collet 18 and cannot move relative to collet 18. The inner diameter of hollow collet shaft 16 is slightly greater than the inner diameter of collet 18 such that when collet 18 is open, a lead or device body is free to slide in an axial direction with respect to collet 18 and shaft 16. The size of collet 18 is determined by the size of the lead or device body with which the delivery system is to be used. Thus the overall diameter of the collet and closing member assembly 15 may be made very small when used with a small diameter lead or other device.

Figure 4:
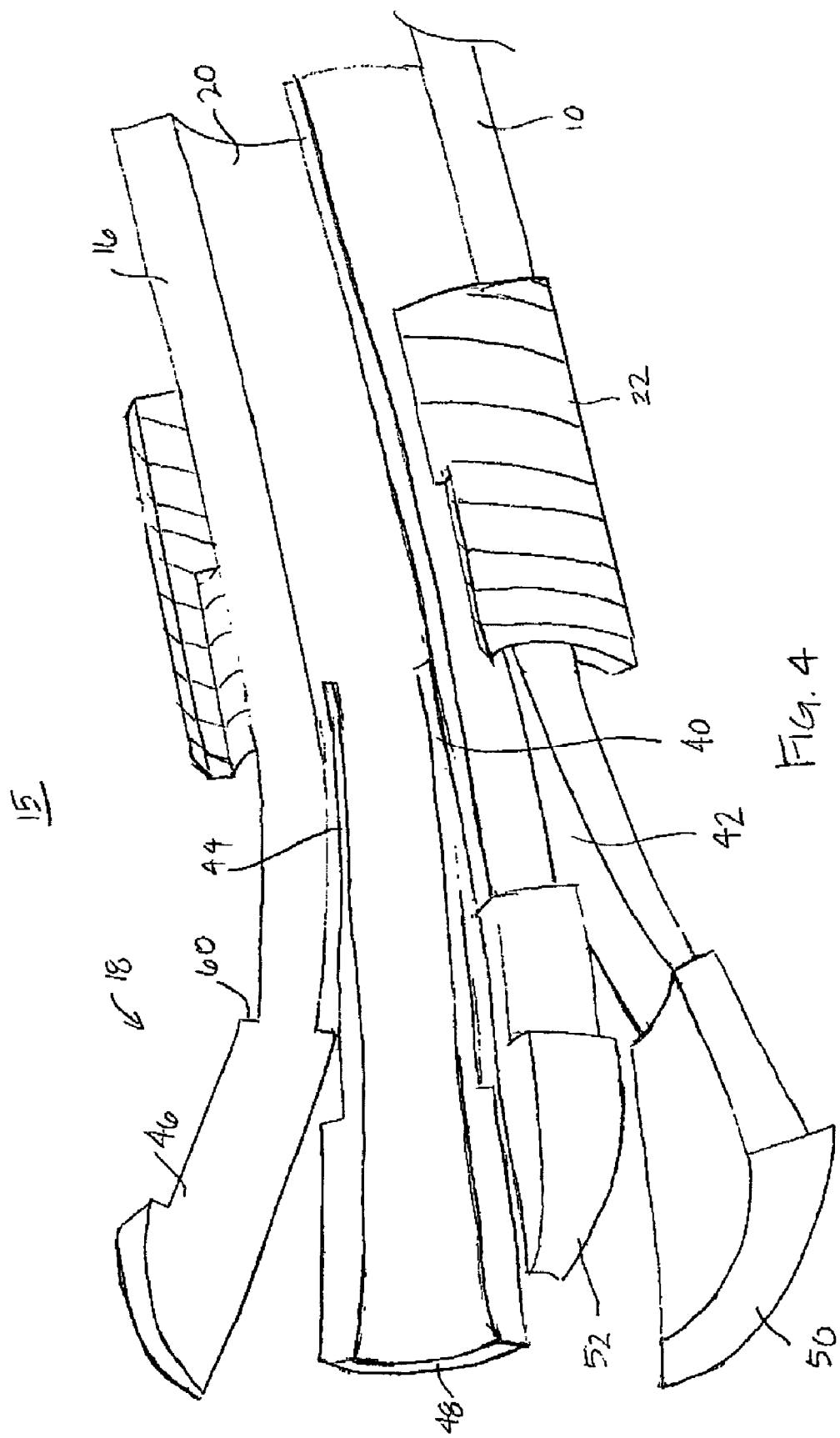
FIG. 4 is a perspective view of the collet and closing member assembly of FIG. 3 wherein the collet is shown in an open position.

FIG. 4 is a perspective view of the collet and closing member assembly wherein the collet is shown in an open position. Collet 18 is provided with shape memory preferably causing collet 18 to have a normally open position. When closing member 22 is retracted to a position as shown in FIG. 4, channels 40, 42 and 44 widen, separating parting members 46, 48, 50 and 52 such that collet 18 resiliently flares to an open position as shown in FIG. 4. Axial movement of closing member 22 is restricted in the distal direction by proximally facing lateral shoulder 60, extending in a radially outward direction from parting members 46, 48, 50 and 52.

Axial movement of closing member 22 is restricted in the proximal direction by the distal end of guide body 10. When closing member 22 is fully retracted by actuating retraction member 26 (not visible in FIG. 4), member 22 is flush against the distal end of guide body 10, allowing collet 18 to gain a fully open position. When closing member 22 is fully advanced by actuating retraction member 26, member 22 is flush against proximally facing lateral shoulder 60, causing collet 18 to close as shown previously in FIG. 3.

FIG. 5 is a plan view of the delivery system of FIG. 1 in which the collet and closing member assembly is closed around a cardiac lead body. The cardiac lead 100 includes a lead body 102 carrying a tip electrode 104, a ring electrode 106, and a defibrillation coil electrode 108. Lead 100 may include additional electrodes or other sensors in alternative embodiments. Each electrode 104, 106 and 108 is coupled to a corresponding conductor extending through lead body 102 to proximal connector assembly 110. Connector assembly 110 includes a connector pin 112 that is coupled to the conductor corresponding to tip electrode 104. Connector assembly 110 further includes two connector rings 114 and 116 each coupled to a conductor corresponding to ring electrode 106 and coil electrode 108, respectively. Three sets of sealing rings 118 are provided for forming a fluid tight seal with a connector bore on an associated implantable medical device and for preventing fluid leakage between connector pin 112, connector rings 114 and 116.

Lead 100 is mounted in collet 18 by inserting lead body 102 through longitudinal opening 20 and aligned opening 24 of closing member 22. Lead 100 may alternatively be threaded through the proximal open end of hollow shaft 16 and advanced into collet 18 a desired distance. An entire length of the lead body 102 remains exposed, including defibrillation coil electrode 108, allowing electrophysiological measurements to be made while lead 100 is carried by the delivery system. Guide body 10 may be provided with a proximal retaining member 62 for holding lead body 102 adjacent the proximal end of guide body 10 and preventing lead body 102 from becoming twisted around guide body 10.

FIG. 6 is a plan view of the delivery system and cardiac lead of FIG. 5 in which the collet is in an open position around the cardiac lead body. Closing member 22 is in a fully retracted position, flush against the distal end of guide body 10. With actuating member 28 pulled in a proximal direction, retraction member 26 extends from the proximal end of guide body 10. Collet 18 flares to its normal, fully open position such that the collet and closing member assembly 15 may slide easily over lead body 102.

Figure 7:
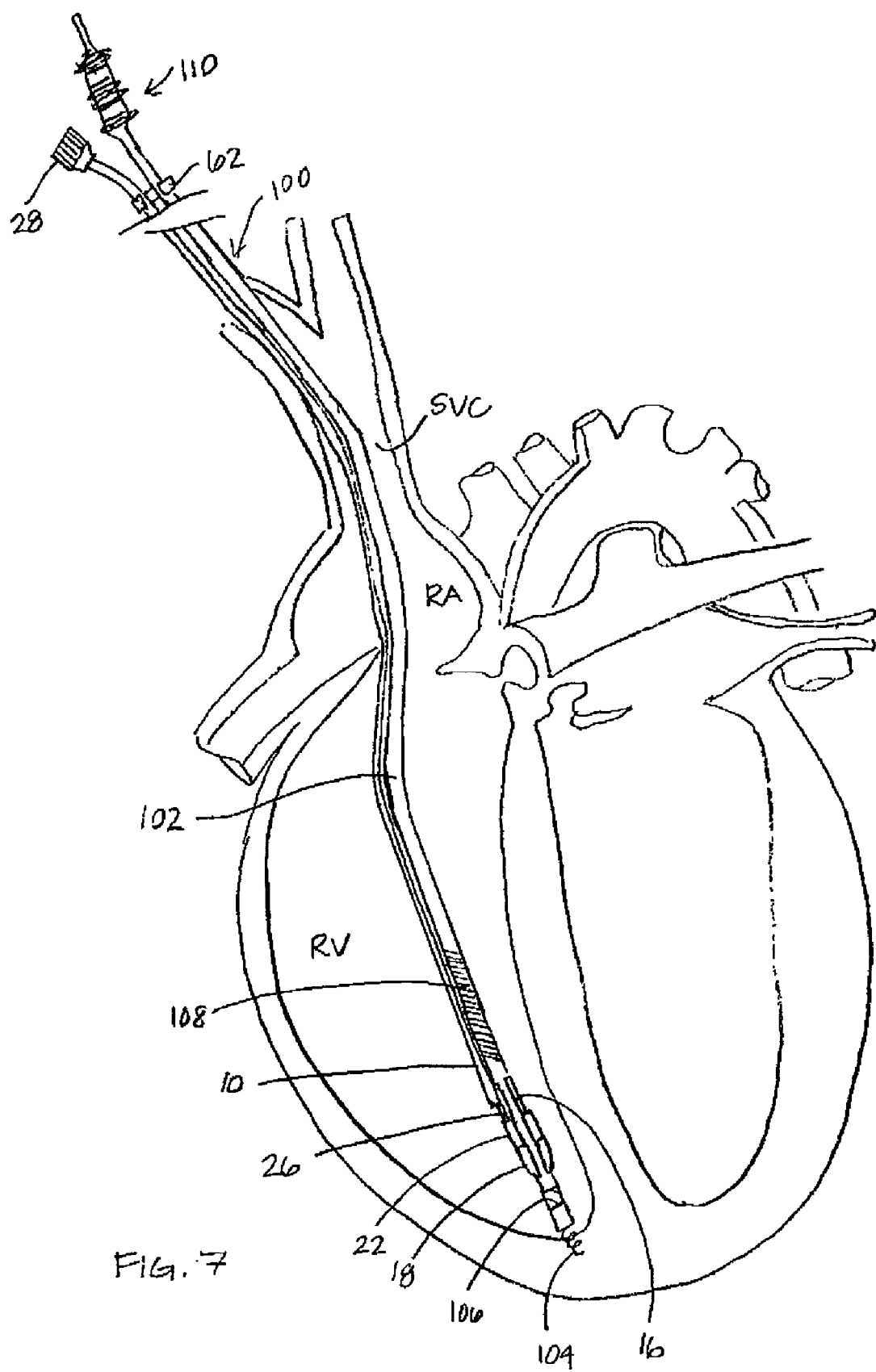
FIG. 7 is an illustration of a patient's heart showing a cardiac lead being deployed using the delivery system of FIG. 1.

FIG. 7 is an illustration of a patient's heart showing a cardiac lead being deployed using the delivery system of FIG. 1. A distal portion of cardiac lead body 102 is mounted in the collet and closing member assembly. Using guide body 10, the distal end of lead 100 has been advanced to the apex of the right ventricle (RV) via the superior vena cava (SVC) and right atrium (RA). Guide body 10 may be used to transfer axial or torsional force for fixing the distal lead end, depending on the type of fixation mechanism present, if any. Guide body 10 advantageously provides a linear or near linear torque transfer, similar to some sheath-based delivery systems, which may be used for fixing a lead at a desired location. Such effective torque transfer is generally not possible with guidewires or stylets that may be used for guiding a lead to an implant site.

Lead 100 is shown having a helical fixation electrode 104. Rotation of guide body 10 at its proximal end allows helical tip electrode 104 to be fixed into the endocardial tissue. During this rotation, retaining member 62 maintains the position of lead body 102 adjacent to guide body 10 and prevents twisting of lead body 102 around guide body 10.

The cardiac lead may alternatively be provided with other types of active or passive fixation mechanisms. For example, a barb or hook type of fixation device may be provided and engaged within the cardiac tissue by applying the appropriate forces to guide body 10. A cardiac lead may also be provided with a retractable fixation helix or a fixation mechanism that may require rotation of the lead body to engage the fixation mechanism, in which case collet 18 may be opened to allow the lead body to be rotated to fix the lead in place. Passive fixation members, such as tines, may protrude from the distal lead end. Tines may be held against the lead body by collet 18 during lead deployment, thereby preventing the tines from catching or snagging on anatomical structures as the lead is advanced or retracted through a vascular pathway. Opening of collet 18 would allow the tines to extend and fix the lead position, for example by pressing against the walls of a vessel lumen or engaging the ventricular trabeculae.

Once the cardiac lead is positioned, electrophysiological measurements, such as pacing, defibrillation, or sensing threshold measurements, may be made to determine if the lead placement is acceptable. Once determined acceptable, the delivery system may be removed.

Figure 8:
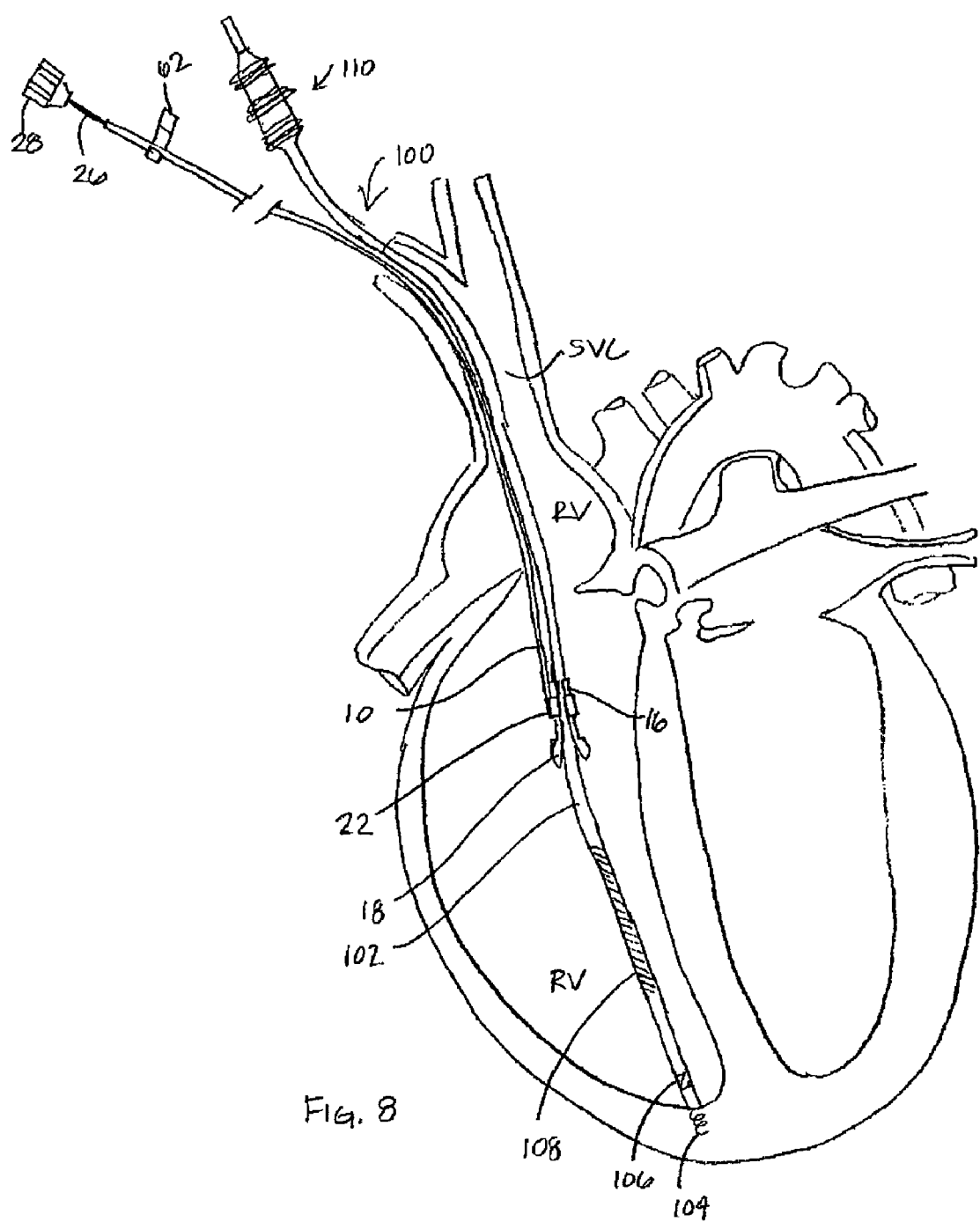
FIG. 8 is an illustration of a patient's heart showing removal of the delivery system of FIG. 7 after the lead has been positioned in the patient's heart.

FIG. 8 is an illustration of a patient's heart showing removal of the delivery system of FIG. 7 after the lead has been positioned in the patient's heart. Actuation member 28 has been pulled in a proximal direction to retract retraction member 26 and closing member 22, thereby opening collet 18. With collet 18 open, the collet and closing member assembly may be withdrawn in a proximal direction over lead body 102. Lead body 102 has been released from retaining member 62 at its proximal end allowing guide body 10 to be withdrawn from the heart and patient's body while cardiac lead 100 remains implanted. Removal of the delivery system is completed by removing lead body 102 from the collet and closing member assembly through longitudinal opening 20. Removal of the delivery system is thus performed quickly and easily; no slitting of the guide body or additional tools are required. The risk of lead dislodgment, which can occur when removing slittable sheath-based delivery systems, is minimized because the removal of the delivery system is well-controlled by the physician, after the system is completely removed from the patient's body.

If the lead position is determined to be unsatisfactory after the delivery system has been removed, the delivery system may be reused to reposition the lead 100. The collet and closing member assembly may be reinserted over lead body 102 near the proximal connector assembly 110 and, with collet 18 in an open position, slid over lead body 102 toward the distal end of lead 100. Collet 18 may then be closed by pushing on actuation member 28 of retraction member 26. Traction or rotational force applied to the proximal end of guide body 10 may be used to remove the distal end of lead 100 from its fixed location, and lead 100 may be repositioned using guide body 10 to guide the advancement of lead 100 to a new location. Once lead 100 is finally positioned, the delivery system may be reused to deliver additional leads or other devices of a similar size as desired.

A delivery system provided by the present invention may further be used for tunneling the proximal end of a lead under the skin so that it may be connected to an associated implantable medical device, such as a pacemaker or implantable cardioverter defibrillator. The proximal connector assembly of a chronically implantable lead generally needs to be tunneled to a subcutaneous pocket wherein an associated medical device will be implanted. A delivery system for performing this task may be provided having adequate guide body stiffness to push through subcutaneous tissue and an appropriately sized collet and closing member assembly to fit over a lead connector assembly. The shape of the distal end of the collet may be provided such that the collet may be easily advanced through the subcutaneous tissue. For example, the collet may be generally pointed or may be provided with a relatively sharp tip. The collet and closing member assembly may be inserted over the proximal connector assembly of a lead to tunnel it subcutaneously to an associated device. The collet may then be opened and the delivery system withdrawn over the lead body.

Figure 9:
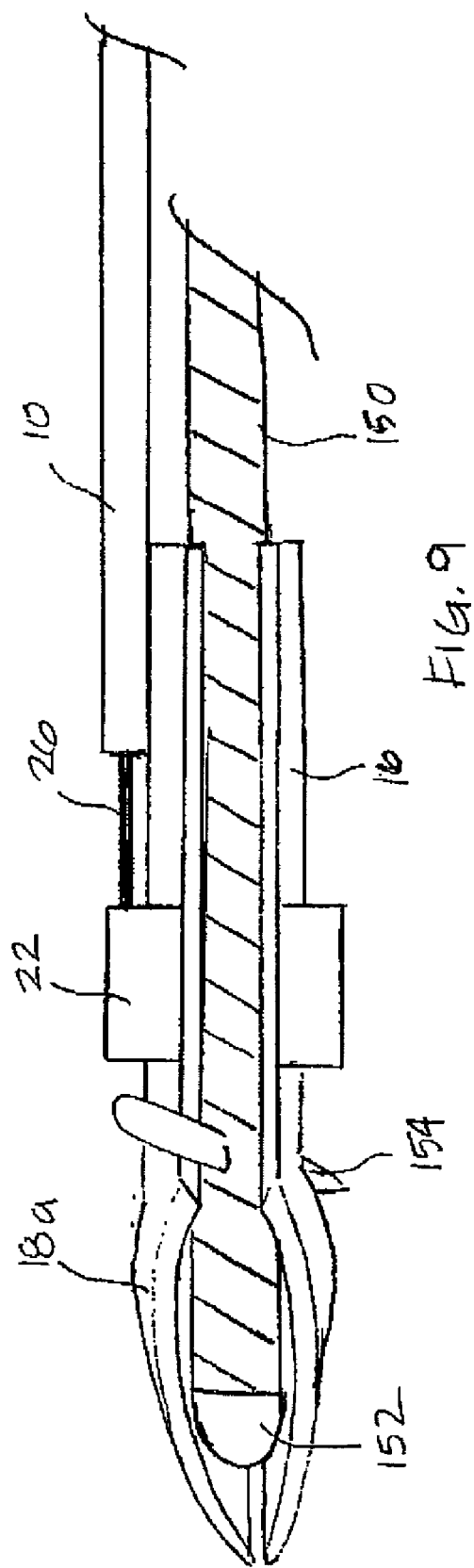
FIG. 9 is an alternative embodiment of non-sheath based delivery system including a collet having a sharpened or hypodermic needle-like tip for use in positioning a medical device at a depth in a tissue.

FIG. 9 is an alternative embodiment of non-sheath based delivery system including a collet having a pointed or hypodermic needle-like tip for use in positioning a medical device at a depth in a tissue. Identically numbered components shown in FIG. 9 correspond to those shown in FIG. 1, however, in this case, collet 18*a* is provided with a pointed tip, rather than a "bullet nose" tip, such that it may be used as a stab-in device for positioning the tip of a lead or other device at a depth within a targeted tissue site.

A cardiac lead is shown mounted in the collet and closing member assembly in FIG. 9. The cardiac lead includes a lead body 150, a tip electrode 152 and a curved fixation hook 154 encircling a portion of the lead body circumference. A lead having a fixation mechanism of this type is disclosed in U.S. Pat. No. 4,799,499 to Bisping and U.S. Pat. No. 5,443,492, issued to Stokes, et al., both patents incorporated herein by reference in their entirety. Longitudinal opening 20 through collet 18*a* and shaft 16 allow hook 154 to be exposed to surrounding tissue. A medical device used with a delivery system including the "stab-in" type collet as shown in FIG. 9 may be provided with numerous types of fixation mechanisms other than a curved fixation hook such as a dagger, barb, tine or other member.

Guide body 10 may be advanced to a desired location and axial force may be applied to guide body 10 to cause collet 18*a* to pierce into the targeted tissue site. For example, it may be desirable to place a lead or device tip at a depth within the myocardial tissue, either from an endocardial or epicardial approach or into the ventricular or atrial septum.

Figure 10:
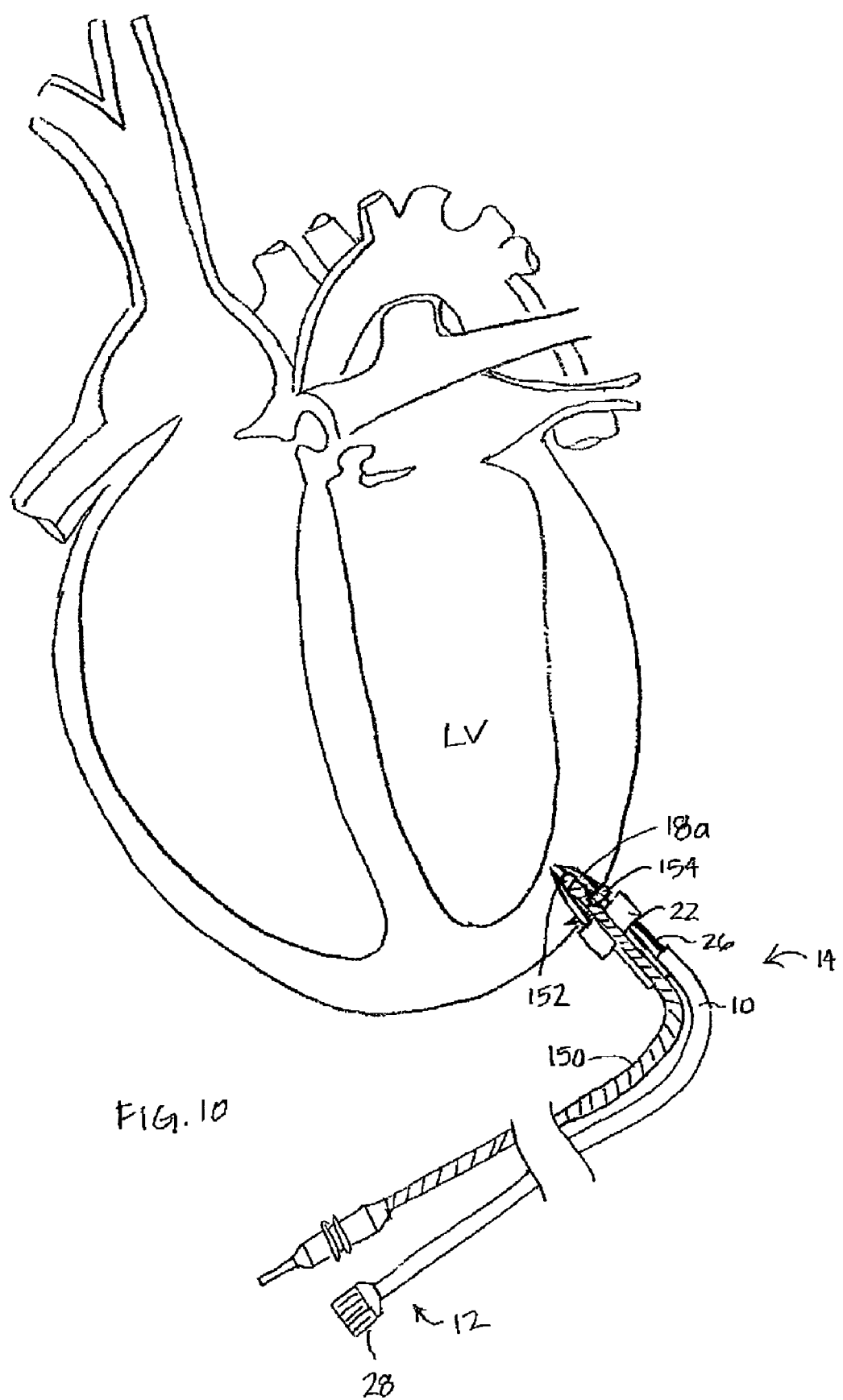
FIG. 10 is an illustration of a patient's heart showing an epicardial lead being deployed using a delivery system having the stab-in collet shown in FIG. 9.

FIG. 10 is an illustration of a patient's heart showing an epicardial lead being deployed using a delivery system having the stab-in collet of FIG. 9. In order to achieve effective left ventricular pacing, it may be necessary in some patients to implant an epicardial electrode on the surface of the left ventricle. This process normally requires a thoracotomy and is generally invasive. The delivery system of FIG. 9 may be used to ease this process and reduce the invasiveness of the procedure by using the guide body 10 to direct the lead to a desired position on the left ventricle through a minimally-sized incision.

Using the stab-in collet 18*a*, the tip electrode 152 may be inserted into the myocardial tissue of the. left ventricle (LV) until hook 154 is adjacent the epicardial surface. Rotation of guide body 10 will cause hook 154 to engage in the myocardium, thus fixing the lead at the implant site.

Figure 11:
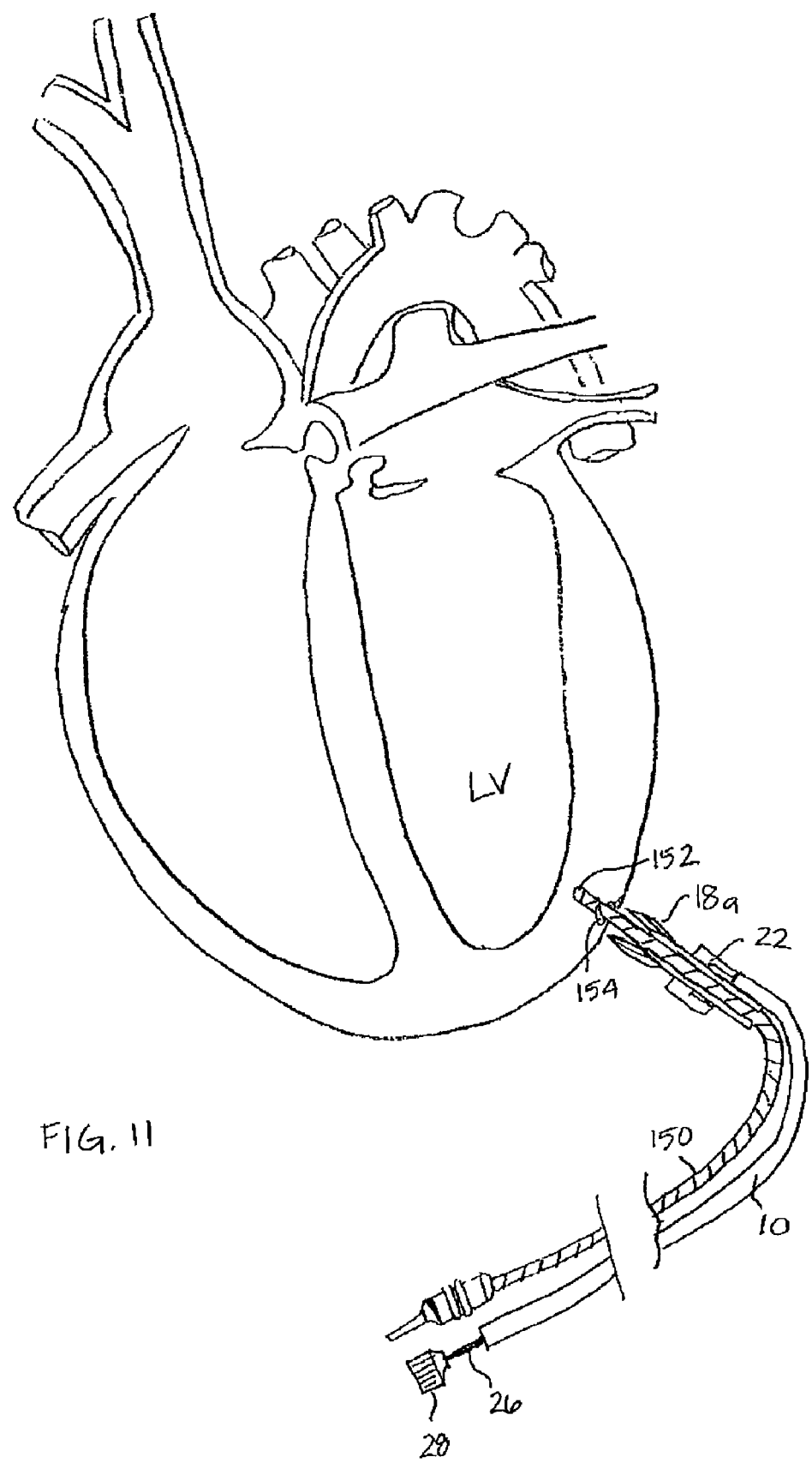
FIG. 11 is an illustration of a patient's heart showing the delivery system of FIG. 10 being removed after placing the epicardial lead on the left ventricle.

FIG. 11 is an illustration of a patient's heart showing the delivery system of FIG. 10 being removed after placing the epicardial lead on the left ventricle. Collet 18*a* is opened by retracting closing member 22 using actuation member 28 to pull retraction member 26 in a proximal direction, in the manner described previously. The collet 18*a* and closing member 22 assembly may then be withdrawn over lead body 150 so that the delivery system may be removed from the cardiac lead, while the lead remains fixed at the implant site.

FIG. 12 is a plan view of an alternative embodiment of a collet and closing member assembly wherein the closing member is rotatable with respect to the collet and collet shaft. In this embodiment, identically labeled components correspond to the components shown in FIG. 1 however closing member 22*a* is rotatable with respect to collet 18 and shaft 16. Rotation of closing member 22*a* over longitudinal opening 20 may be used as a mechanism for retaining a lead or other device within the collet and closing member assembly 15, particularly when collet 18 is in an open position. Rotation of closing member 22*a* with respect to collet 18 and shaft 16 may be achieved by providing a thread 80 on the inner diameter of closing member 22*a* and an associated thread guide 82 on the outer diameter of shaft 16. Alternatively, a thread could be provided on the outer diameter of shaft 16 and a thread guide could be provided on the inner diameter of closing member 22*a*.

FIG. 13 is a side view of closing member 22*a* showing thread 80 extending along a portion of the inner circumference of closing member 22*a*. FIG. 14 is a plan view of the collet and closing member assembly 15 of FIG. 12 wherein the closing member 22*a* has been advanced axially to close collet 18 and to at least partially close longitudinal opening 20. As closing member 22*a* is advanced over collet 18, closing member 22*a* will rotate with respect to shaft 16 as thread 80 tracks on guide 82 (shown in FIG. 12). Longitudinal opening 20 is partially closed by closing member 22*a*. Retraction member 26 will extend from guide body 10 and is flexible enough to wind partially around shaft 16.

In alternative embodiments rotation of closing member 22*a* may be accomplished by rotating the proximal end of retraction member 26. In this case, lumen 30, previously shown in FIG. 2A as a generally square lumen, is preferably provided as a generally round lumen in order to allow rotation of a retraction member 26 within lumen 30. In yet another embodiment, rotation of closing member 22*a* could be achieved by providing a portion of the distal end of retraction member 26 with shape memory such that it winds around shaft 16 when it is not contained within guide body 10. Thus, when retraction member 26 is advanced from the distal end of guide body 10 to advance closing member 22*a* over collet 18, retraction member 26 winds partially around shaft 16 causing rotation of closing member 22*a* to a position similar to that shown in FIG. 14.

FIG. 15 is a partially cut-away, side view of an alternative embodiment of a delivery system wherein the retraction member is provided as a spring-loaded member. Identically labeled components shown in FIG. 15 correspond to those in the delivery system of FIG. 1; however, in this embodiment retraction member 26 is fixedly attached to a movable anchor 92 located within guide body lumen 30. Movable anchor 92 is movable in an axial direction with respect to guide body 10. A fixed anchor 94 is held at a fixed location within lumen 30, proximal to movable anchor 92. Fixed anchor 94 may be fixedly attached to the walls of lumen 30 or retained by a radially-inward extending annular shoulder 96, a groove in the wall of lumen 30 or other retaining mechanism. Anchors 92 and 94 may be ring shaped members and are provided for anchoring opposite ends of a coiled spring 90 extending between anchor 92 and anchor 94. Retraction member 26 extends through the center of coiled spring 90. Spring 90 attains its normal, non-compressed length when closing member 22 is advanced over collet 18 by extending retraction member 26 in a distal direction.

FIG. 16 is a partially cut-away, side view of the delivery system of FIG. 15 showing the spring member 90 in a compressed state. Retraction member 26 is pulled proximally using actuation member 28 to retract closing member 22 and allow collet 18 to open. As retraction member 26 is pulled proximally, movable anchor 92, attached to retraction member 26, moves proximally with retraction member 26 causing spring 90 to become compressed between movable anchor 92 and fixed anchor 94. As long as tension is applied to retraction member 26, closing member 22 remains in a retracted position with collet 18 open. If actuation member 28 is released, spring 90 extends to its normal length causing closing member 22 to advance over and close collet 18. Thus collet 18 is maintained in a closed position on a medical device unless actuation member 18 is actively retracted, preventing collet 18 from inadvertently being left open and moving relative to the device body.

Spring 90 could be attached directly to the proximal end of guide body 10 eliminating the need for a fixed anchor 94 and directly to retraction member 26 at its distal end eliminating the need for a movable anchor 92. Movable anchor 92, fixed anchor 94 and intervening spring 90 are shown to be located within the proximal end of guide body 10 in FIGS. 15 and 16. However, spring 90 could be located any where along the length of guide body 10 and retraction member 26. For example, the proximal end of spring 90 could alternatively be attached to a fixed anchoring point at the distal end of guide body 10 such that spring 90 extends over retraction member 26 outside of guide body 10 to a movable anchoring point on retraction member 26, at or near the distal end or retraction member 26. Alternatively, the distal end of spring 90 could be mounted to a fixed anchoring point at the proximal end of guide body 10, and the proximal end of spring 90 mounted to a movable anchoring point on the proximal end of retraction member 26.

FIG. 17 is a side, partially cut-away view of an alternative embodiment of a collet and closing member assembly that may be included in the delivery system of FIG. 1. Identically numbered components in FIG. 17 correspond to those shown in FIG. 1, however, in this case collet 18b is formed from a resilient polymer, such as silicone rubber or polyurethane. Collet 18b is provided with a fixed inner diameter and an expanding outer diameter moving from the proximal end of collet 18b toward its distal tip.

FIG. 18 is a side, partially cut-away view of the collet and closing member assembly of FIG. 17 in a closed position. Advancement of closing member 22 onto the ramped outer diameter of collet 18b compresses the outer diameter causing a reduction in the inner diameter. The reduced inner diameter of collet 18b will squeeze down on the body of a device carried in the delivery system, holding the device securely within collet 18b.

FIG. 19 is a plan view of an alternative embodiment of the delivery system of the present invention in which the guide body is further equipped with a pull wire to aid in steering the delivery system along a tortuous pathway. Identically numbered components shown in FIG. 19 correspond to those shown in FIG. 1, however, in this case, guide body 10a is provided with a flexible distal segment 70 that is relatively more flexible than the remainder of guide body 10a. Flexible distal segment 70 may be formed by providing helical cuts or corrugations in the material used to manufacture guide body 10a. If guide body 10a is formed from stainless steel, distal segment 70 may be annealed to create a more flexible segment. If guide body 10a is formed from a polymeric material, flexible segment 70 may be formed from a lower durometer polymer than the remainder of guide body 10a.

FIG. 20 is a cross-sectional view of the guide body included in the delivery system shown in FIG. 19. Guide body 10a may be provided as a bilumen tubular body in which one lumen 30 carries retraction member 26 and a second lumen 72 carries a pull wire 74 that is fixedly attached at or near the distal end of guide body 10a. Alternatively, pull wire 74 and retraction member 26 may extend through a single lumen guide body. Pull wire 74 extends the entire length of guide body 10a and exits the proximal end where it may be provided with a proximal handle 76.

FIG. 21 is a plan view of the delivery system of FIG. 19 showing deflection of the distal end of the guide body using a pull wire. Pulling on proximal handle 76 to apply tension on pull wire 74 will cause flexible segment 70 to be deflected to allow the guide body 10a to be steered around obstacles encountered as the delivery system is advanced through a tortuous pathway. A steering mechanism employing a pull wire that may be adapted for use in the present invention is disclosed in U.S. Pat. No. 5,873,842 issued to Brennen et al., incorporated herein by reference in its entirety.

Steerability of guide body 10 may also be provided by incorporating thermal or electrically activated shape memory material near the distal end of guide body 10 that, when activated, causes the flexible distal segment 70 to deflect in a desired direction. A selectively activated shape memory device that could be adapted for use in the present invention is disclosed in U.S. Pat. No. 6,072,154 issued to Maynard, incorporated herein by reference in its entirety.

Figure 22:
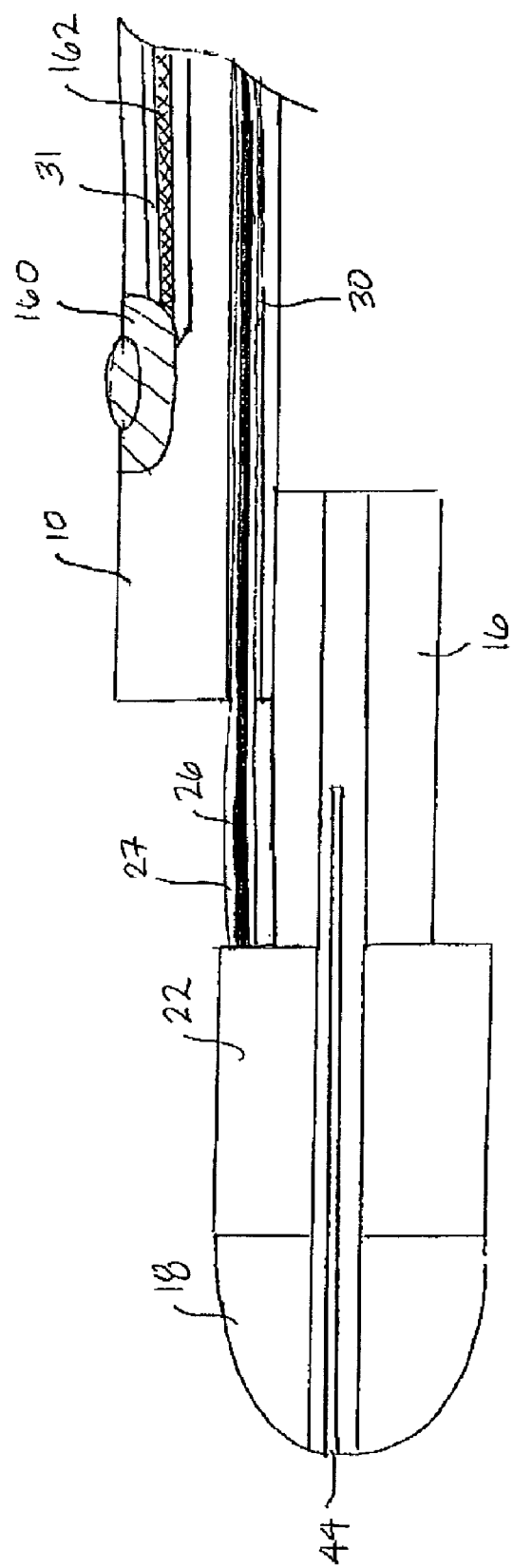
FIG. 22 is a partially cut-away side view of a delivery system including a sensor carried by the guide body and a closing member that may also serve as an electrode.

FIG. 22 is a partially cut-away side view of a delivery system including a sensor carried by the guide body and a closing member that may also serve as an electrode. The delivery system may include electrodes or other sensors that may be used alternatively or in addition to any sensors or electrodes located on the device being delivered. In the embodiment of FIG. 22, closing member 22 may also serve as an electrode with retraction member 26 also serving as an electrical conductor. In this embodiment, closing member 22 and retraction member 26 are formed from an electrically conductive material, such as stainless steel. Retraction member 26 is provided with insulation 27, which may be a coating or tubular sheath formed form an insulating material such as silicone, polyurethane, polytetrafluoroethylene, ethylene tetrafluoroethylene, or Parylene. If shaft 16 and collet 18 are also formed from a conductive material, the inner diameter and distal and proximal ends of closing member 22, which may be in contact with other conductive components, may also be coated with an insulating material such as Parylene. A connector assembly could be added to the proximal end of retraction member 26 or a conductive clamp, connected to an external monitor such as an ECG monitor, could be attached to the proximal end of retraction member 26.

Electrodes or sensors could additionally or alternatively be carried by the guide body 10. In FIG. 22, a sensor 160, which may be an electrode, a pressure sensor, an oxygen sensor etc., is shown positioned near the distal end of guide body 10 and coupled to a conductor 162 carried in a second guide body lumen 31. Thus, depending on the number of sensors carried by guide body 10, guide body 10 may be provided as a multilumen body. Guide body 10 may also carry additional electrodes coupled to conductors arranged concentrically or in a multifilar coil. A concentric conductor arrangement is described in U.S. Pat. No. 4,355,646 issued to Kallok, incorporated herein by reference in its entirety. A multifilar coiled conductor is described in U.S. Pat. No. 4,944,088 issued to Doan, et al, incorporated herein by reference in its entirety.

FIG. 23 is an exploded view of the distal end of a delivery system according to an alternative embodiment of the present invention in which the components are provided as interlocking components. Identically labeled components in FIG. 23 correspond to those shown in FIG. 1, however, in this embodiment shaft 16 of collet 18 is provided with an engaging member 170 for interlocking with a corresponding keyed groove 172 provided on guide body 10. Thus, the collet shaft 16 may be fixedly attached to guide body 10 by an interlocking mechanism rather than welding, bonding or other methods. The interlocking system components could be provided pre-assembled or alternatively be provided unassembled. Unassembled components could advantageously be provided in a kit wherein a selection of collets having different shaped tips is included. Various shaped collets could include the bullet-nose tipped collet shown in FIG. 1, the stab-in collet shown in FIG. 9, or other shapes such as a collet having a generally cylindrical tip for coring or boring, a hook-shaped tip for engaging in tissue or an anatomical structure, etc. Thus a physician may select a collet appropriate for the task to be performed at the time of a surgical procedure and attach the selected collet by interlocking the collet shaft with the guide body.

To assemble the interlocking components shown in FIG. 23, the shaft 16 is inserted through closing member 22 in the direction of arrow 180. Shaft 16 may be rotated as necessary to pass engaging member 170 through longitudinal opening 24 of closing member 22. Shaft 16 may then be rotated to interlock engaging member 170 with corresponding groove 172. Engaging member 170 and groove 172 may be provided in numerous geometries that provide a secure locking mechanism, which will prevent movement of shaft 16 relative to guide body 10 during a delivery procedure. An engaging member could additionally or alternatively be provided on guide body 10 with a corresponding receiving groove provided on shaft 16.

FIG. 24 is a plan view of the distal end of an alternative embodiment of delivery system having interlocking components. In this embodiment, the collet and closing member assembly 15 may be provided unassembled from the retraction member 26 and guide body 10 such that a selection of differently sized collet and closing member assemblies may be provided. A physician may select from a range of collet and closing member assemblies wherein the collets are provided with different internal diameters for use with differently sized medical devices.

The closing member 22 may be provided already mounted on the collet 18 such that closing member 22 and shaft 16 are simultaneously assembled onto retraction member 26 and guide body 10, respectively. Alternatively closing member 22 may be provided separately from collet 18 and shaft 16 such that the system may be assembled in a two step procedure wherein shaft 16 is assembled onto guide body 10 in one step and closing member 22 is assembled onto retraction member 26 in another step.

Retraction member 174 is provided with a keyed shape 174 at or near its distal end, which corresponds to a keyed shape bore 176 on closing member 22. The closing member 22 and retraction member 26 may be assembled by inserting retraction member 26 into bore 176 until keyed shape 174 fixedly engages within bore 176. Numerous types of interlocking mechanisms may be provided on retraction member 26 and closing member 22 to form a secure locking mechanism between retraction member 26 and closing member 22. Collet shaft 16 and guide body 10 may be assembled by inserting engaging member 170 into corresponding groove 172 as described previously.

The interlocking components provided in the systems shown in FIGS. 23 and 24 may be provided such that once assembled, the components cannot be disassembled. Alternatively, the interlocking components may be provided such that they may be disassembled to allow more than one collet size or shape to be used during a single procedure.

Thus, a non-sheath based medical device delivery system has been described for advantageously introducing a specialized medical device maintaining exposure of an entire length of the device body, allowing electrodes or sensors positioned along the body of the device to be operational during an implantation procedure. The overall diameter of the delivery system may be minimized so that it may be used with small diameter leads or other medical devices. The system may easily be removed from medical devices having bulky proximal connector assemblies and may be reused for delivering multiple devices during a single procedure or repositioning a lead or device without removing the device from the patient's body. Numerous variations to the embodiments described herein may be conceived by those knowledgeable in the art, therefore, the descriptions provided herein are to be considered exemplary, not as limiting, with regard to the following claims.

What is claimed is:

1. A medical device deployment system comprising:
an elongated medical device configured for implantation and having a proximal end and a distal end with a first axis extending therebetween;
a resilient collet;
a closing member in cooperative engagement with the collet;
an elongated tubular guide structure having a proximal end and a distal end with a second axis defined therebetween, wherein the distal end is attached to a portion of the collet; and
a retraction member having a proximal end and a distal end, the distal end being attached to the closing member and the proximal end exiting said proximal end of the elongated tubular guide structure and wherein actuation of the retraction member moves the closing member to a first position and actuating the retraction member in an opposite direction moves the closing member to a second position, where the collet includes a first longitudinal opening configured to receive the elongated medical device when the closing member is in the first position so that the resilient collet is in an open position and when the closing member is in the second position and the resilient collet is in a closed position the elongated medical device is retained within the first longitudinal opening so that the first axis of a portion of the elongated medical device retained by the collet is generally parallel to the second axis of the guide structure proximate the collet.

2. The system of claim 1, wherein the collet further includes at least two separating elements at the distal end form a resilient flaring structure.

3. The system of claim 2, wherein said resilient flaring elements adjust to various opening sizes at the distal end.

4. The system of claim 3, wherein said closing member movably enables adjustment of said opening sizes.

5. The system of claim 2, wherein said resilient flaring elements form a generally dome-like structure at the distal end.

6. The system of claim 5, wherein said flaring elements form a hypodermic needle-like tip.

7. The system of claim 5, wherein said flaring elements include a tipped conical structure.

8. The system of claim 5, wherein said flaring elements form a tipped shape including one of and a combination of a geometric shape and multiple geometric shapes.

9. The system of claim 5 wherein said flaring elements are separated by at least one gap extending longitudinally therefrom.

10. The system of claim 1 and further comprising a second longitudinal opening disposed along the closing member.

11. The system of claim 10, wherein the first longitudinal opening and the second longitudinal opening are aligned with one another so as to facilitate the reception of an elongated medical device.

12. The system of claim 1, wherein the elongated medical device is retained within the first longitudinal opening and moveable longitudinally with respect to the guide structure when the resilient collet is open and the elongated medical device is retained within the first longitudinal opening and prevented from moving with respect to the guide structure when the collet is closed.

13. The system of claim 1, wherein the elongated medical device is a lead.

14. The system of claim 1, wherein the closing member includes a second longitudinal opening that is aligned with the first longitudinal opening when the closing member is in the first position and is out of alignment with the first longitudinal opening when the closing member is in the second position such that a portion of the closing member occludes a portion of the first longitudinal opening.

15. The system of claim 1, wherein the elongated medical device includes a proximal end and a distal end and is securable within the collet proximate the distal end of the elongated medical device such that the elongated medical device can be delivered by manipulation of the elongated tubular guide, wherein the elongated medical device remains substantially unoccluded.

16. The system of claim 15, wherein sensors positioned along the medical device are operable and functional within a patient when the distal end of the medical device is secured to the collet.

17. The system of claim 16, wherein the elongated medical device is substantially unoccluded when secured by the collet.

18. The system of claim 1, wherein the resilient collet is separable from a remainder of the system.

19. The system of claim 18, further comprising multiple interchangeable collets.

20. The system of claim 19, wherein one interchangeable collet forms a generally dome-like structure in a closed position and a second interchangeable collet forms a needle-like structure in a closed position.

21. The system of claim 19, wherein each interchangeable collet has an internal diameter sized to retain a particular medical device having an external diameter matched to the internal diameter.

22. The system of claim 21, wherein the multiple interchangeable collets each have different internal diameters.

23. The system of claim 15, further comprising a proximal clamp disposed on the tubular guide structure for securing a proximal portion of the elongated medical device.

24. The system of claim 1, further comprising:
a lumen disposed within the guide structure; and
a pull wire disposed within the lumen to effectuate bending of the guide structure.

25. The system of claim 24, wherein the lumen has a rectangular cross section and the pull wire has a rectangular cross section.

26. The system of claim 24, where the lumen has a circular cross section and the pull wire has a circular cross section.

27. The system of claim 1, wherein the guide structure includes at least one helical groove to increase the flexibility of a portion of the guide structure.

28. The system of claim 1, wherein the guide structure includes a deformable section.

29. The system of claim 28, wherein the deformable section is formed from a shape memory alloy.

30. The system of claim 28, wherein the deformable section is formed from a malleable material that can be selectively manipulated to hold a configuration.

31. The system of claim 28, wherein the deformable section includes at least one helical groove.

32. The system of claim 1, wherein an elongated medical device is selectively and repeatably securable within the collet.

33. The system of claim 1, wherein the elongated tubular guide structure is sufficiently rigid to facilitate steerable deployment within a body structure with an elongated medical device secured within the collet.

34. The system of claim 1, further comprising a biasing portion disposed along the retraction member for biasing the closing member into the first position.

35. The system of claim 34, wherein the biasing portion includes;
a moveable anchor coupled to a first portion of the retraction member;
a fixed anchor coupled to a second portion of the retraction member that is proximal to the first portion;
a spring coupled between the moveable anchor and the fixed anchor.

36. The system of claim 1, further comprising a sensor disposed on the tubular guide structure.

37. The system of claim 36, wherein the sensor is an electrode.

38. The system of claim 1, further comprising a sensor disposed on the collet.

39. The system of claim 1, further comprising a sensor disposed on the closing member.

40. The system of claim 1, wherein the medical device includes a body portion receivable with the collet and an end portion attached to the body portion that is larger than the body portion.

41. A method of implanting an elongated medical device comprising:

positioning a distal portion of the elongated medical device within a collet of a deployment tool having an elongated body, such that the elongated medical device is held external to and adjacent to the tool;

guiding the deployment tool to a desired location;

opening the collet;

retracting the tool, wherein the open collet slides along the medical device; and separating the collet from the medical device by withdrawing a proximal portion of the medical device from a longitudinal groove disposed on the collet.

42. The method of claim 41, wherein the tool is intact after separating the collet from the medical device.

43. The method of claim 41, further comprising:

reattaching the collet to the proximal portion of the medical device;

advancing the tool along the medical device until the collet is proximate the distal portion of the medical device;

closing the collet so that the medical device is coupled with the tool.

44. The method of claim 41, wherein guiding the tool includes passing the tool through a vein.

45. The method of claim 41, wherein guiding the tool includes passing the tool through tissue.

46. The method of claim 45 further comprising stabbing the tool to gain initial entry into the tissue.

47. The method of claim 41, further comprising:

selecting a collet having a shape appropriate for a desired deployment; and connecting the collet to the elongated body.

48. The method of claim 41, further comprising:

positioning a distal portion of a second elongated medical device within the collet of the deployment tool, such that the second elongated medical device is held external to and adjacent to the tool;

guiding the deployment tool to a desired location;

opening the collet;

retracting the tool, wherein the open collet slides along the second medical device; and separating the collet from the second medical device by withdrawing a proximal portion of the medical device from a longitudinal groove disposed on the collet.

49. A method of implanting an epicardial lead, comprising:

attaching a distal portion of the epicardial lead to heart tissue;

positioning a proximal portion of the epicardial lead within a collet of a deployment tool having an elongated body, such that the epicardial lead is held external to and adjacent to the tool;

tunneling the deployment tool to a pocket created for holding an implantable medical device connectable to the epicardial lead;

opening the collet;

retracting the tool; and separating the collet from the epicardial lead by withdrawing a distal portion of the epicardial lead from a longitudinal groove disposed on the collet.

* * * * *